(12) United States Patent
Bisch et al.

(10) Patent No.: US 6,179,829 B1
(45) Date of Patent: Jan. 30, 2001

(54) FOOT CONTROLLER FOR MICROSURGICAL SYSTEM

(75) Inventors: Michael Evremonde Bisch, St. Louis; Bruce Robert Cochran, St. Charles; Christopher Michael Eberhardt, Florissant; Stanley Curtis McFerran, Imperial; John A. Painter, Bridgeton; Michael Andrew Wagner, University City, all of MO (US)

(73) Assignee: Bausch & Lomb Surgical, Inc., Claremont, CA (US)

( * ) Notice: Under 35 U.S.C. 154(b), the term of this patent shall be extended for 0 days.

(21) Appl. No.: 08/919,989

(22) Filed: Aug. 28, 1997

(51) Int. Cl.[7] ............................. H01R 24/00; A61B 17/00
(52) U.S. Cl. ........................ 606/1; 200/51.02; 200/51.03; 200/51.05; 200/86.5
(58) Field of Search ................................. 700/83, 84, 40, 700/17, 75, 172; 600/118, 126; 128/920; 606/46, 40, 1; 200/51.02, 51.03, 51.05, 86.5

(56) References Cited

U.S. PATENT DOCUMENTS

| | | | |
|---|---|---|---|
| 3,742,167 | 6/1973 | Muther | 200/86.5 |
| 3,809,454 | * 5/1974 | Brambring | 359/182 |
| 3,980,848 | 9/1976 | Schulz | 200/86.5 |
| 3,980,849 | 9/1976 | Straihammer | 200/86.5 |
| 3,983,344 | 9/1976 | Straihammer | 200/86.5 |

(List continued on next page.)

OTHER PUBLICATIONS

Oertli Orbit VC890300 Victrectomy Control Unit—User's Manual Date—Prior to Aug. 28, 1986 7 Pages.
Oertli Orbit VC890100 Irrigation/Aspiration Control Unit—User's Manual Date—Prior to Aug. 28, 1986 14 Pages.
Oertli Orbit VC890200 Ultrasound Phaco Unit—User's Manual Date—Prior to Aug. 28, 1986 12 Pages.
Oertli Orbit VC890400 Universal Diathermy Unit—Use's Manual Date—Prior to Aug. 28, 1986 13 Pages.

Primary Examiner—Paul P. Gordon
Assistant Examiner—Iván Calcaño
(74) Attorney, Agent, or Firm—Grant D. Kang

(57) ABSTRACT

A foot control assembly for a microsurgical system for controlling a plurality of ophthalmic microsurgical instruments connected thereto. The microsurgical instruments are for use by a user such as a surgeon in performing ophthalmic surgical procedures.

The system includes a data communications bus and a user interface connected to the data communications bus. The user interface provides information to the user and receives information from the user which is representative of operating parameters of the microsurgical instruments.

The system also includes surgical modules connected to and controlling the microsurgical instruments as a function of at least one of the operating parameters. The surgical modules are also connected to the data communications bus.

The data communications bus provides communication of data representative of the operating parameters between the user interface and the surgical modules. Other features are also disclosed including a main control, an endo-illuminator system, a phacoemulsification handpiece, surgical scissors, a vitrectomy cutter, a surgical foot control, a remote control, a cart.

24 Claims, 20 Drawing Sheets

Microfiche Appendix Included
(15 Microfiche, 3032 Pages)

U.S. PATENT DOCUMENTS

| Patent No. | Date | Inventor | Class |
|---|---|---|---|
| 4,019,514 | 4/1977 | Banko | 128/230 |
| 4,122,853 | 10/1978 | Smith | 128/303.1 |
| 4,156,187 | 5/1979 | Murry et al. | 324/142 |
| 4,180,074 | 12/1979 | Murry et al. | 128/276 |
| 4,180,812 | 12/1979 | Kaltenbach et al. | 340/706 |
| 4,200,106 | 4/1980 | Douvas et al. | 128/305 |
| 4,383,167 | 5/1983 | Gmeinder et al. | 377/2 |
| 4,395,258 | 7/1983 | Wang et al. | 604/65 |
| 4,417,875 | 11/1983 | Matsui | 433/101 |
| 4,428,748 | 1/1984 | Peyman et al. | 604/22 |
| 4,493,695 | 1/1985 | Cook | 604/27 |
| 4,493,698 | 1/1985 | Wang et al. | 604/51 |
| 4,516,063 | 5/1985 | Kaye et al. | 318/685 |
| 4,523,911 | 6/1985 | Braetsch et al. | 433/101 |
| 4,553,958 | 11/1985 | LeCocq | 604/67 |
| 4,554,917 | 11/1985 | Tagnon | 128/303.1 |
| 4,564,018 | 1/1986 | Hutchison et al. | 128/660 |
| 4,580,557 | 4/1986 | Hertzmann | 128/303.1 |
| 4,622,503 | 11/1986 | Sundblom et al. | 318/645 |
| 4,626,248 | 12/1986 | Scheller | 604/319 |
| 4,627,833 | 12/1986 | Cook | 604/34 |
| 4,639,710 | 1/1987 | McMillan et al. | 338/108 |
| 4,642,769 | 2/1987 | Petrofsky | 364/415 |
| 4,650,460 | 3/1987 | Roizenblatt | 604/22 |
| 4,706,687 | 11/1987 | Rogers et al. | 128/752 |
| 4,757,814 | 7/1988 | Wang et al. | 128/318 |
| 4,758,220 | 7/1988 | Sundblom et al. | 604/65 |
| 4,768,506 | 9/1988 | Parker et al. | 128/303 R |
| 4,770,654 | 9/1988 | Rogers et al. | 604/22 |
| 4,790,816 | 12/1988 | Sundblom et al. | 604/31 |
| 4,798,535 | 1/1989 | Nielsen | 433/101 |
| 4,798,580 | 1/1989 | DeMeo et al. | 604/30 |
| 4,837,857 | 6/1989 | Scheller et al. | 455/617 |
| 4,838,281 | 6/1989 | Rogers et al. | 128/752 |
| 4,867,155 | 9/1989 | Isaacson | 128/305 |
| 4,933,843 | 6/1990 | Scheller et al. | 364/413.01 |
| 4,983,901 | 1/1991 | Lehmer | 318/685 |
| 4,995,877 | 2/1991 | Ams et al. | 606/180 |
| 5,077,506 | 12/1991 | Krause | 318/71 |
| 5,091,656 * | 2/1992 | Gahn | 307/119 |
| 5,108,389 | 4/1992 | Cosmescu | 606/10 |
| 5,157,603 * | 10/1992 | Scheller et al. | 606/4 |
| 5,166,513 | 11/1992 | Keenan et al. | 250/221 |
| 5,169,215 * | 12/1992 | Takata | 303/113.4 |
| 5,237,891 | 8/1993 | Neubquer | 74/560 |
| 5,249,121 | 9/1993 | Baum et al. | 364/413.01 |
| 5,268,624 | 12/1993 | Zanger | 318/551 |
| 5,324,900 | 6/1994 | Gonser et al. | 200/86.5 |
| 5,332,298 * | 7/1994 | Fujioka | 303/20 |
| 5,340,953 | 8/1994 | Krebs et al. | 200/86.5 |
| 5,351,676 | 10/1994 | Putman | 128/4 |
| 5,422,521 | 6/1995 | Neer et al. | 307/119 |
| 5,423,231 | 6/1995 | Helfrich et al. | 74/561 |
| 5,461,355 | 10/1995 | Schemansky et al. | 338/108 |
| 5,515,478 | 5/1996 | Wang | 395/86 |
| 5,524,180 | 6/1996 | Wang et al. | 600/118 |
| 5,549,139 | 8/1996 | Perkins et al. | 137/884 |
| 5,554,894 | 9/1996 | Sepielli | 307/119 |
| 5,578,040 | 11/1996 | Smith | 606/41 |
| 5,580,347 | 12/1996 | Reimels | 604/30 |
| 5,595,344 | 1/1997 | Starnes | 239/307 |
| 5,597,146 | 1/1997 | Putman | 248/276.1 |
| 5,635,777 | 6/1997 | Telymonde et al. | 307/119 |
| 5,689,159 | 11/1997 | Culp et al. | 318/254 |
| 5,700,147 | 12/1997 | Mills et al. | 433/98 |
| 5,712,460 | 1/1998 | Carr et al. | 200/86.5 |
| 5,754,741 | 5/1998 | Wang et al. | 395/86 |
| 5,787,760 | 8/1998 | Thorlakson | 74/512 |
| 5,797,467 * | 8/1998 | Watanabe | 180/271 |
| 5,810,765 | 9/1998 | Oda | 604/31 |
| 5,883,615 * | 3/1999 | Fago et al. | 345/156 |
| 6,033,035 * | 3/2000 | Neumann et al. | 303/113.4 |

* cited by examiner

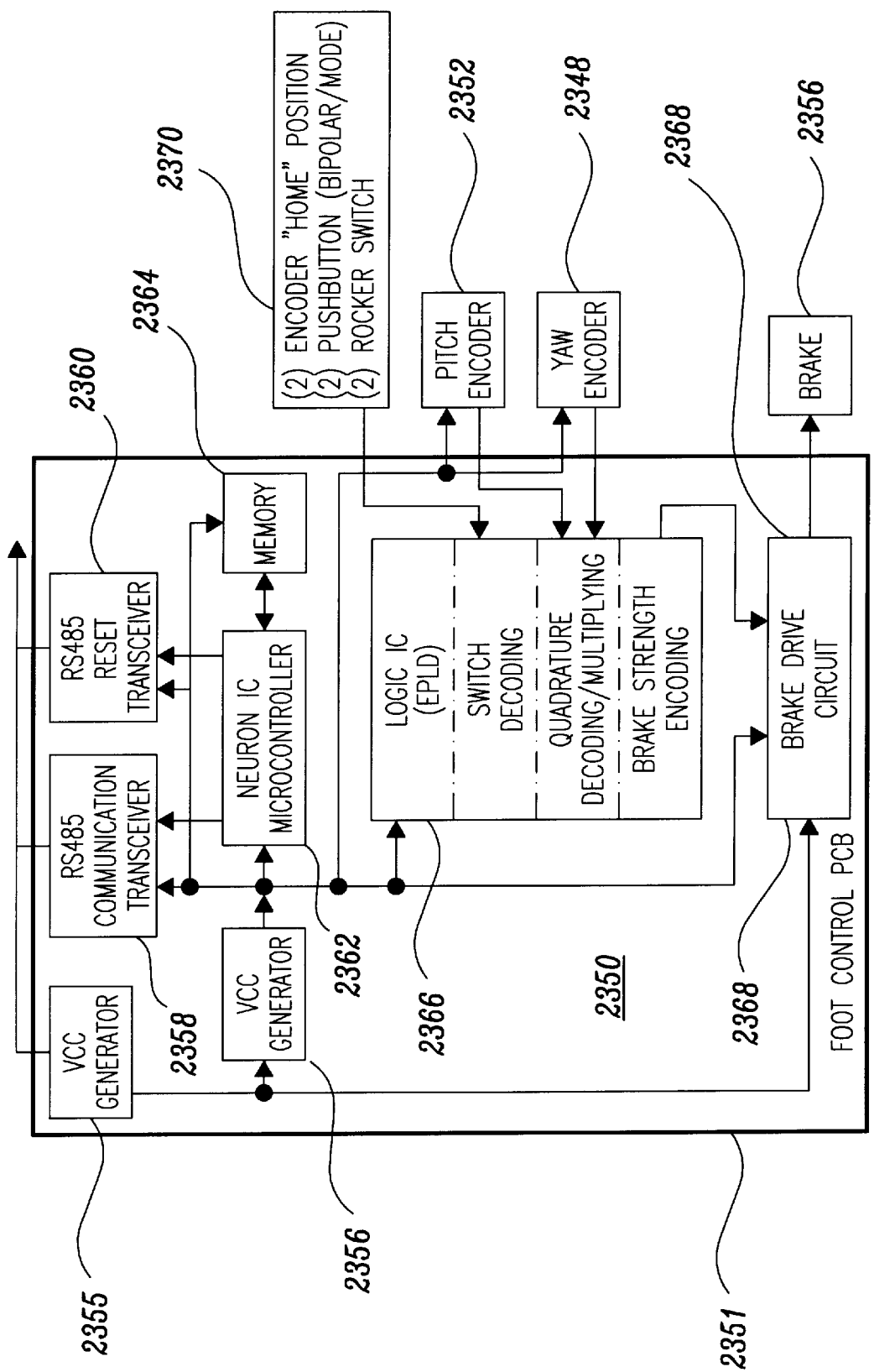

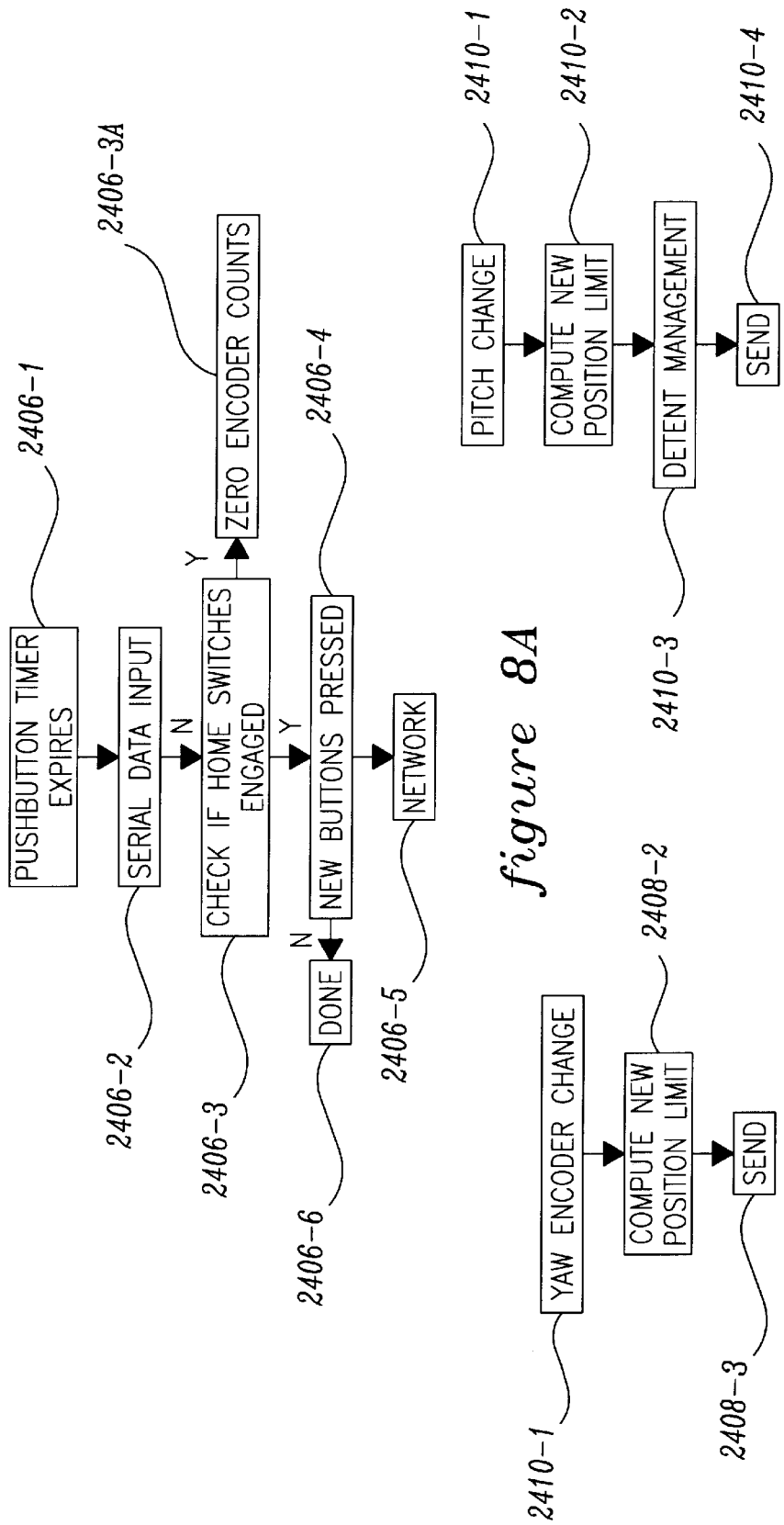

FOOT CONTROLLER FOR MICROSURGICAL SYSTEM

MICROFICHE APPENDIX

This application includes a microfiche appendix having 15 microfiches and 3032 frames which is a copy of the provisional application under which priority was claimed.

BACKGROUND OF THE INVENTION

The invention relates to the control of surgical instruments, especially microsurgical and ophthalmic systems, by the use of foot controls, and more particularly, to a surgical foot control, namely a peripheral foot control assembly 15, with programmable features and functions for specific use in a modular microsurgical system for anterior and posterior ophthalmic surgery as described below, and herein interchangeably as "the modular microsurgical system" or "the microsurgical system" or "the microsurgical control system." As disclosed, such microsurgical system uses a fully modular microprocessor-controlled methodology which allows the system to be dynamically configured electronically for anterior, posterior or both surgical environments from a console of the system. Further, as the present surgical foot control includes microprocessor-controlled circuitry which communicates with the modular microsurgical system, reference may be had, for purposes of a further understanding, to the copending patent application entitled "Ophthalmic Microsurgical System", Serial No. 60/025,498, filed Aug. 29, 1996, for comprehensive disclosure of the software and certain communication bus protocols usable therewith.

In use of a microsurgical multi-functional system as the foregoing, a surgeon conducting surgery or carrying out ophthalmic procedures in the anterior or posterior portions of the eye necessarily will have his or her eyes at a microscopic viewing instrument, and desires to be able to carry out control of the various ophthalmic modules by the use of a foot control of the invention. Such a foot control desirably provides controls not only for the various ophthalmic modules, selecting the surgical mode desired, and controlling the rate of operation produced by handpieces interconnected with the modules, such as aspiration, vitrectomy cutting, phacoemulsification, scissor cutting, and so forth.

Ophthalmic microsurgical systems in present day use, and as have been proposed and used for a number of years in modern ophthalmic surgical practice, have heretofore been controlled by foot controls, as typically may be used in conjunction with a display console.

An example of a modern control system for ophthalmic surgical instruments, employing a foot control, is found in co-assigned U.S. Pat. No. 5,157,603, entitled Control System for Ophthalmic Surgical Instruments and herein called "predecessor system." The foot control in the predecessor system, specifically designed for such system, does not have all the features and advantages of the present foot control. Foot controls disclosed in related co-assigned U.S. Pat. Nos. 5,091,656 and 4,837,857 should also be noted as disclosing features of prior foot controls usable in microsurgical systems for ophthalmic surgery.

Numerous other microsurgical systems using foot controls have been known and used; and indeed simple foot controls have been used for many years in the medical and surgical arts and for other cognate uses where the user desires to be able to use foot control in order to free the hands and in order to obviate need for diversion of the eyes from a task or procedure at hand.

Nevertheless, foot controls as heretofore known are not without considerable drawbacks when it is desired to be able to use the same foot control for controlling a variety of possible devices, ophthalmic tools and instruments; or where it is desired that the same foot control be equally as useful with one type of module as for another, while allowing the foot control to select the mode or module desired, while providing also capability for use of the foot control with any of possible future modules as they become available.

But, in general, prior foot controls have not had the desired degree of flexibility and programmability allowing for the wide gamut of conceivable modes and preferences.

SUMMARY OF THE INVENTION

A specific concern in the use of foot controls for ophthalmic surgery systems is that ophthalmic surgeons may have various different preferences and individual practices or customs in the way in which they want or expect the foot control to perform or operate. Thus, a surgeon may be left-footed or right-footed. In addition to elemental capability for a foot control to allow either left-footed or right-footed use, it is desired that the foot control permit accommodation of various possible differences and preferences in rate, control sensitivity and feedback, as will facilitate surgical preferences in practice in myriad precise and different procedures which may vary from one individual to the next, and there are even differences according to whether a ophthalmic surgeon is performing anterior segment procedures or posterior procedures.

Because the modular microsurgical system is microprocessor controlled, it is also desired that a foot control for such a system provide the capability of receiving, implementing and reporting various signals for system communication in a digital format used by such system.

Thus, it is desirable that a foot control is itself modular, and that it be a "smart control." It is further desired that it use only low voltage, low power circuitry as appropriate for operating room environment, but with the circuitry being capable of interfacing with digital circuits, including a central processor and any of various modules and peripherals, of such a modular microsurgical system as the foregoing. It is desired that the "smart control" have the capability for system communication with such circuits by means of appropriate interface network protocols such as the known RS-485 protocol.

In carrying out various surgical procedures by means of such a system, it is desired that the foot control provide an actuating foot pedal with capability for movement in both pitch and yaw in order to accommodate various possible control actions in accordance with the mode of usage of the system at any given time. Thus, a surgeon can use the pitch control for one or more distinct modes of operation; and the yaw control for one or more other modes of operation.

In pitch control, it is desirable to be able to have the actuating pedal movable within specific regions. Thus, in a first region, a surgeon in an irrigation mode may then be able to move the foot pedal from zero deflection with increasing deflection causing increasing aspiration; and then with further deflection, the foot pedal can be moved through a second region in which a mode such as phacoemulsification or vitrectomy cutting occurs with increasing rate as the pedal is still further deflected in the second region.

It is preferable that the foot control and surgical system in which it is used permit the point of transition from the first region to the second region be electronically selected by the operation of controls. This may be carried out by touch screen control, as made possible by the referenced modular microsurgical system.

Heretofore the definition of such regions and point of transition from one region to the next has been typically inherently defined by the mechanical and electrical characteristics of the foot control, and this does not facilitate changing the point or points of transition.

Moreover, it is important for a surgeon to be able receive tactile feedback, when operating the foot control, as by having a detent, in order readily to perceive the point of transition from one region to the next.

Heretofore, it has been proposed, as in co-assigned Gahn U.S. Pat. No. 5,091,656, to use a mechanical arrangement with multiple springs which can be selective coupled in or out of engagement for purposes of tactile feedback, dependent upon mode of usage.

Existing foot controls are primarily dedicated in their function and operation to a specific system or type of equipment. In this sense these known foot controls have fixed functions. Thus, they typically merely incorporate switches and other "dumb circuits" hard-wired for a specific usage, lack modular capability required for such a modular microsurgical system, and lack the capability of allowing electronic programmability or reprogrammability of the system as to the extent of such foot pedal ranges, and the extent or magnitude of tactile sensation to be provided by the foot pedal.

Because the modular microsurgical system is not only diverse and versatile in its configuration, so also should the foot control used in such a system be diverse and versatile in its capabilities and in the degree of its range of operation (as for precise control over cutting rates for example) and its degree of sensitivity when used in any of the various possible modes of the system.

Accordingly, among the objects and advantages of the new surgical foot control, namely a peripheral foot control module, as herein described and illustrated, are such a foot control which includes programmable features and functions for specific use in a modular microsurgical system for anterior and posterior ophthalmic surgery;

which will be the primary control input for a surgeon to interact with the modular microsurgical system;

which as so used in such a system provides controls not only for the various ophthalmic modules, but also provides selection of the surgical mode desired, and permits full control of the rate of operation produced by handpieces interconnected with the modules, such as aspiration, vitrectomy cutting, phacoemulsification, scissor cutting, and others as may be used in such a system;

which provides one or more foot pedal linear inputs for surgeon-controlled input to the system; and includes push button-type control elements in addition by means of which the surgeon is given complete control over which function is assigned to the linear input(s);

which provides for such a system capability for use of the foot control with any of possible future modules as they become available for such a system;

which allows a surgeon either left-footed or right-footed use;

which permits accommodation by a surgeon of various possible differences and preferences in rate, control sensitivity and feedback, as will facilitate surgical preferences in practice in myriad precise and different procedures which may vary from one individual to the next, and there are even differences according to whether a ophthalmic surgeon is performing anterior segment procedures or posterior procedures;

which accordingly exhibits free-function programmability and reprogrammability when used in a microsurgical system of the foregoing type, so that its functions can be assigned by preselection of the user; and so that its functions may change as the setup of the microsurgical system changes;

which is fully modular electronically and mechanically;

which provides capability of receiving, implementing and reporting various signals for system communication in a digital format used by a microprocessor-controlled surgical system such as the foregoing;

which communicates by electronic bus protocol with a microprocessor-controlled surgical system such as the foregoing, thereby greatly simplifying interconnection with such system;

which is diverse and versatile in its capabilities and in the degree of its range of operation, as for precise control over cutting rates for example, and its degree of sensitivity when used in any of the various possible modes in a microsurgical multi-functional system as the foregoing, and so allows a surgeon conducting surgery or carrying out ophthalmic procedures in the anterior or posterior portions of the eye out to control precisely and with great versatility various ophthalmic modules by the use of a foot control of the invention;

which provides an actuating foot pedal with capability for movement in both pitch and yaw in order to accommodate various possible control actions in accordance with the mode of usage of the system at any given time;

which incorporates digital encoders for precisely detecting movement of the foot pedal in either or both of its pitch and yaw modes;

which provides the foot pedal user the ability to use pitch control for one or more distinct modes of operation; and the yaw control for one or more other modes of operation;

which provides the foot pedal when used in pitch control with capability of movement within a plurality of specific regions;

which allows the definition of such regions and the point of transition from one region to the next under system-implemented, software-driven display, so as readily to facilitate changing the point or points of transition;

which provides for foot pedal operation such that user will receive tactile feedback, by detent, in order readily to perceive the point of transition from one region to the next; and which creates such detent by electronic means rather than by mechanical devices;

which is essentially electronic in its modes of operation, in sharp comparison to mechanical or other "dumb circuits" hard-wired for a specific usage;

which incorporates ergonomic design of such a high degree as to impart intrinsically to the surgeon-user a completely instinctive, natural type of operation for achieving and facilitating control to a hitherto unachieved degree.

BRIEF DESCRIPTION OF THE DRAWINGS

FIG. 5 is a circuit schematic block diagram of circuitry of the foot control of the invention;

FIGS. 6A–6F together show a detailed circuit schematic diagram of foot control circuitry, in which: FIG. 6A is a detailed circuit schematic diagram of microprocessor features of the circuitry; FIG. 6B is a detailed circuit schematic diagram of EPLD circuitry used with the circuitry of FIG. 6A; FIG. 6C is a detailed circuit schematic diagram of certain reset circuitry used with the circuitry of FIG. 6A; FIG. 6D is a detailed circuit schematic diagram of certain RS-485 circuitry used with the circuitry of FIG. 6A for bus communication with a modular microsurgical system with which the foot control is used; FIG. 6E is a detailed circuit schematic diagram of a power supply for powering the above circuits; and FIG. 6F is a detailed circuit schematic diagram of certain brake drive circuitry of the foot control, as controlled by the circuitry of FIG. 6A;

FIGS. 8A–8C together illustrate main events in the operation of the foot control;

DETAILED DESCRIPTION OF THE INVENTION

Figure 1:
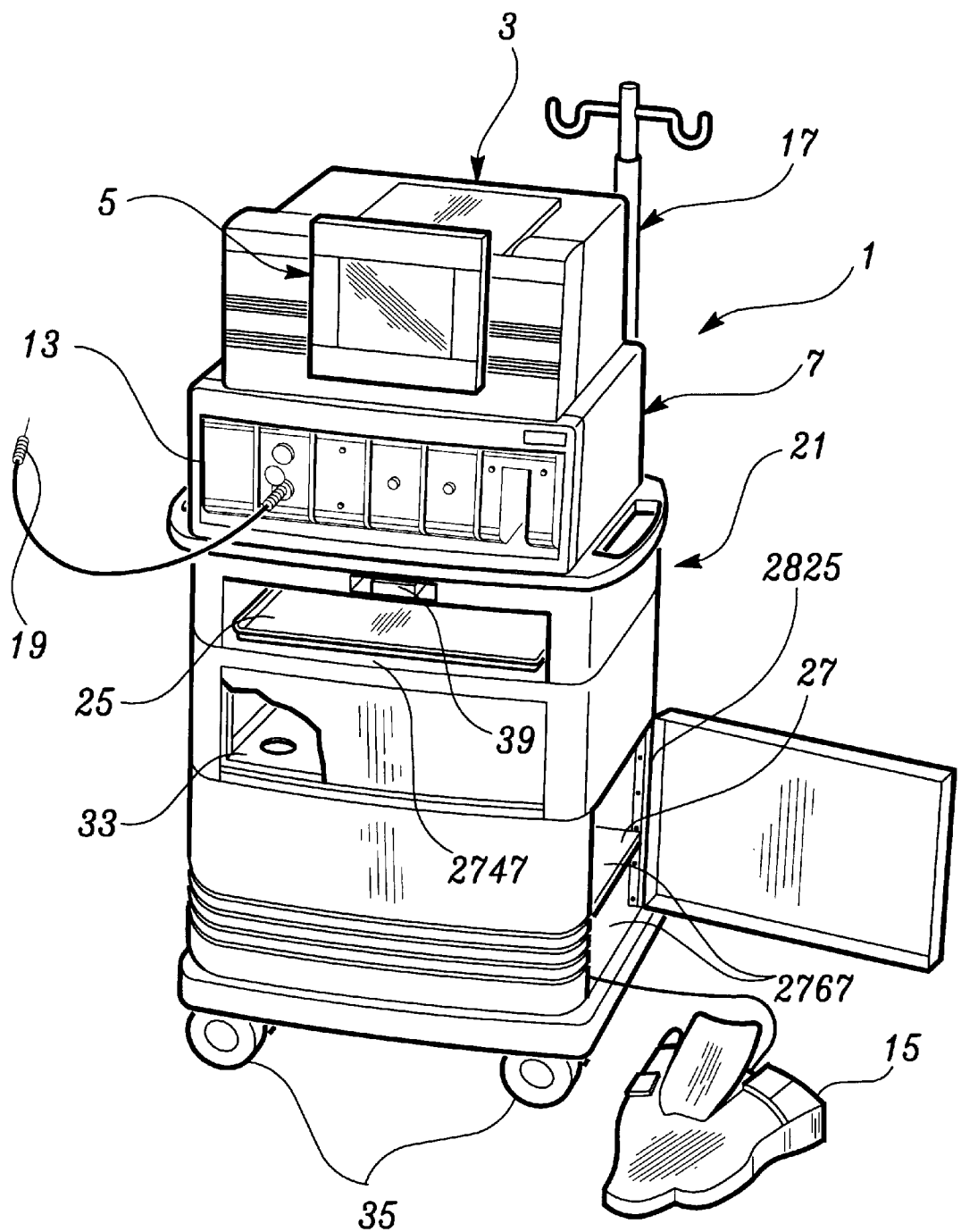
FIG. 1 is a perspective view of a microsurgical control system for use with ophthalmic microsurgical instruments, and having a plurality of control modules, and utilizing a surgical foot control assembly of the present invention.

Referring to the drawings, particularly FIGS. 1—4, foot control assembly 15 constitutes a peripheral foot control which is interconnected with the modular microsurgical control system 1 by means of a cable 2312 which provides bus protocol connection, namely serial RS-485 bus interfacing, and reset signal lines, interconnecting the system and the foot control, and which also provides power, for example, 24 v.d.c. for the foot control and circuitry thereof. By such bus connection 2312, foot control 15 is functionally equivalent to modules 13 with respect to data communications and provides primary control input for a surgeon to interact with the system during ophthalmic procedures by foot control input permitting controlling of the various modules 13 such as any of the various possible ophthalmic modules 13 which are or can be employed in the modular microsurgical system 1. Examples are air/fluid exchange and scissors/forceps module 327, bipolar coagulation and radio frequency diathermy module 329, illumination module 331, irrigation and scroll aspiration module 323 (which includes vitrectomy cutter capability); irrigation, venturi aspiration and vitrectomy module 321; and phacoemulsification and phacoefragmentation module 325. Details of such modules 13 interaction with the microsurgical control system is further disclosed in copending application Serial No. 60/025,498, filed on Aug. 29, 1996, which is hereby incorporated by reference and further disclosed in the Microfiche Appendix of the provisional application attached herewith.

Foot control 15 includes a housing, or console, generally indicated by reference character 2314, as formed preferably of molded material, so as to define an upper surface 2316 sloping to increasing height from a heel portion 2318 toward left and right upper portions 2320, 2322 which define between them an approximately U-shaped recess 2324 in which is presented a center pedal, that is, a foot pedal 2326 of foot-accommodating shape. The foot pedal is dimensionally narrower than recess 2324 so that, as will become apparent, it may be moved from side-to-side in yaw movement by rotation about an shaft assembly 2328 emerging from the walls of recess 2324 and which shaft assembly presents the foot pedal for movement and operation. For assuring of control, the foot pedal is flared upwardly, providing slight flanges 2327, at opposite sides of the foot pedal, which may be apertured as illustrated for lightness and texturing effect tending to make contact by the foot still more secure. The foot pedal 2326 is movable also in pitch, by rocking movement of the shaft assembly, with increasing user pressure upon the pedal in the manner of a vehicular accelerator pedal.

Proximate the heel portion of foot pedal 2326 is a heel rest 2330 in the form of a shallow depression accommodating and resting the heel of the user steadily, i.e., it is a heel recess, whether it be of the left foot or right foot, and permitting precisely controlled movement of the foot pedal in either pitch or yaw modes; and in this regard, establishing a reference point for placing the user's foot upon surface 16 and for relative tactile location of the foot in precise position for operating the foot pedal 2326.

Preferably, it is desired that the foot pedal 2326 be movable through pitch movement of 15° about the pitch axis defined by shaft assembly 2328, with the limits of movement defined mechanically such that the initial elevation is 15° from horizontal; and fully depressed, final elevation is 0° relative to horizontal. A suitable spring return, as later discussed, is included for return to the initial elevation (home position) if the foot is lifted from the pedal. No mechanical detenting is used; but instead programmable detents are created by circuit operation to be described, to include both forward and rearward detent action.

Figure 2:
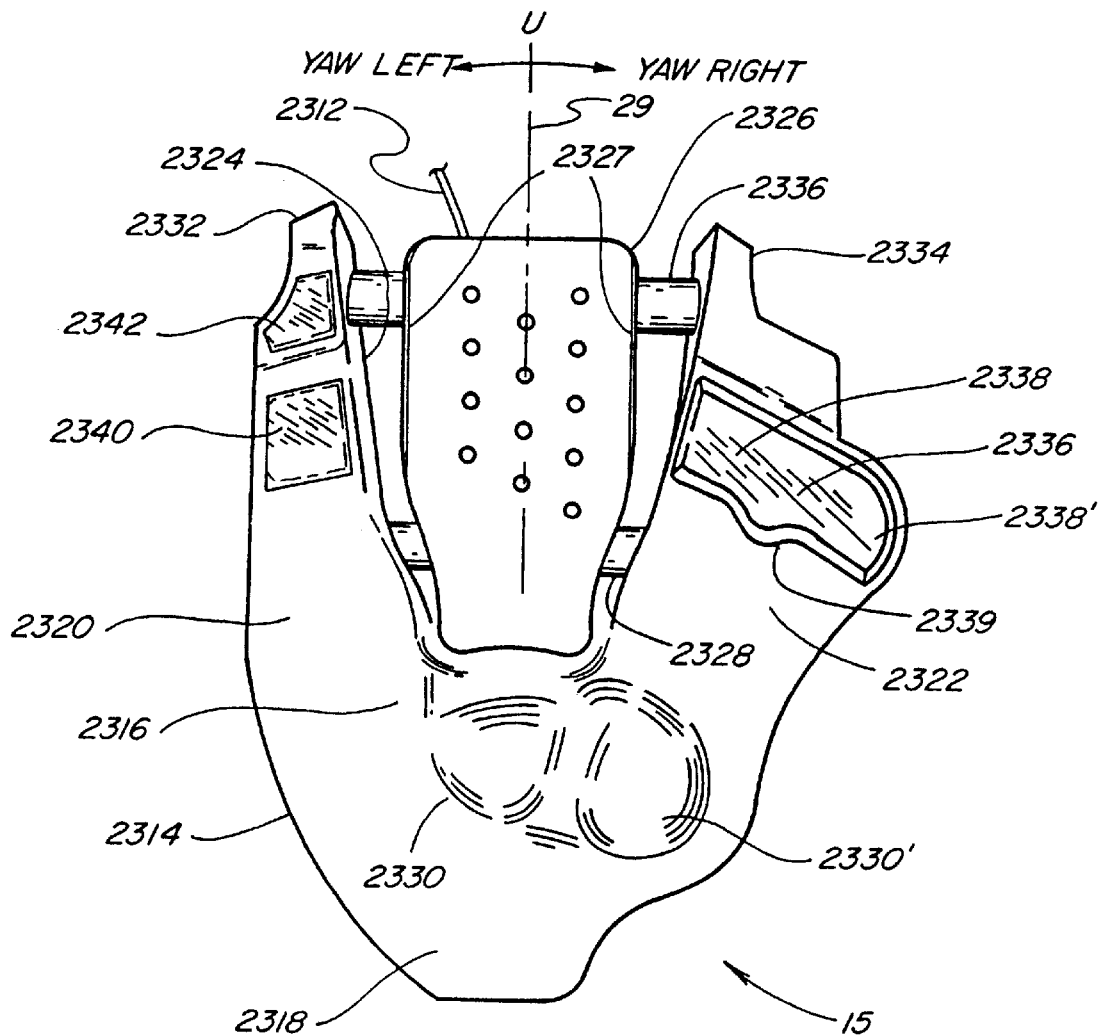
FIG. 2 is a top plan of a peripheral foot control of the microsurgical system, referred to in its entirety as a foot control assembly, or simply foot control, in accordance with a preferred embodiment.

Preferably also, it is desired that the foot pedal 2326 be swingable in yaw through rotation about a yaw axis defined by shaft assembly 2328 such that 10° of travel is permitted from the nominal center position illustrated, and with spring return to the center position, and center detenting being provided mechanically, with operation such that linear control will be provided by movement of the user in the direction of the instep of the control, relative to center, and movement in the opposite direction may by comparison be binary, as for switching on and off of aspiration. In FIG. 2, the yaw possibilities are illustrated by the legends YAW LEFT and YAW RIGHT, about a centerline 2329.

Left and right upper portions 2320, 2322 of the housing define corresponding outer narrow projections 2332, 2334 between which extend a handle 2336 preferably formed integrally with the one-piece housing 2314 which can be used for lifting the foot control assembly 15 and for storing the unit on an instrumentation cart 21 of the microsurgical system 1.

As will appear, cable 2312 emerges from housing 2314 beneath foot pedal 2326 and handle 2336 and interconnects by appropriate plug arrangement (e.g. connector 157) with the microsurgical system 1. Cable 2312 accordingly provides a power supply and communication bus connection with the microsurgical system 1 so that foot control 15, with its own microprocessor circuitry (e.g., control circuit 105 in FIGS. 31A–31J), as will be apparent from the microsurgical system 1 explanation hereinabove, constitutes a node on the bus. Thus the foot control circuitry constitutes nodes on a computer network established by the microsurgical system of FIG. 1. The computer network provides power distribution and peer-to-peer data communication between the nodes, including foot control 15.

Mounted within right upper portion 2322 of the housing surface is a rocker switch 2336 having left and right actuating surfaces 2338, 2338' for momentary actuation upon pressing either actuating surface 2338 or 2338' about the center portion of the rocker switch as denoted by a slight projection 339. Thus, surfaces 2338 or 2338' will be selectively pressed by the user's foot for purposes presently appearing, and preferably include switch-defining tactile feedback by snap action.

Rocker switch 2336 is programmable when used with the microsurgical system of FIG. 1 so as to provide up/down, increment/decrement, or on/off controls for all applicable functions of the system. Thus it may be regarded as an alternate position binary switch device, functioning according to which of its surfaces are selectively pressed.

To the right of heel rest 2330 is a corresponding, similar shallow depression providing a heel rest 2330' for resting and precisely locating the heel when a surgical user desires to operate rocker switch 2336.

Thus, the heel recesses 2330, 2330' within the upper surface of the housing 2314 define for the user the pedal-operating and rocker switch-operating positions, permitting tactile placement of the foot without visual ascertainment.

Mounted within left upper portion 2320 of the housing surface are a mode button 2340, and above it, a bipolar button 2342, both being of momentary actuation type switches with tactile feedback. The mode button is used by the surgeon to select a mode of operation, for example, as to selection of a module 13 or to change of operation of module 13 from one mode to another. Thus, the mode switch selects operation modes by the microsurgical system 1. The bipolar button, coated in the color blue to contrast with the overall different color, e.g., gray, of the foot control housing, is selectively pressed by the surgeon to cause bipolar coagulation operation by an ophthalmic handpiece.

General Internal Features

Figure 3:
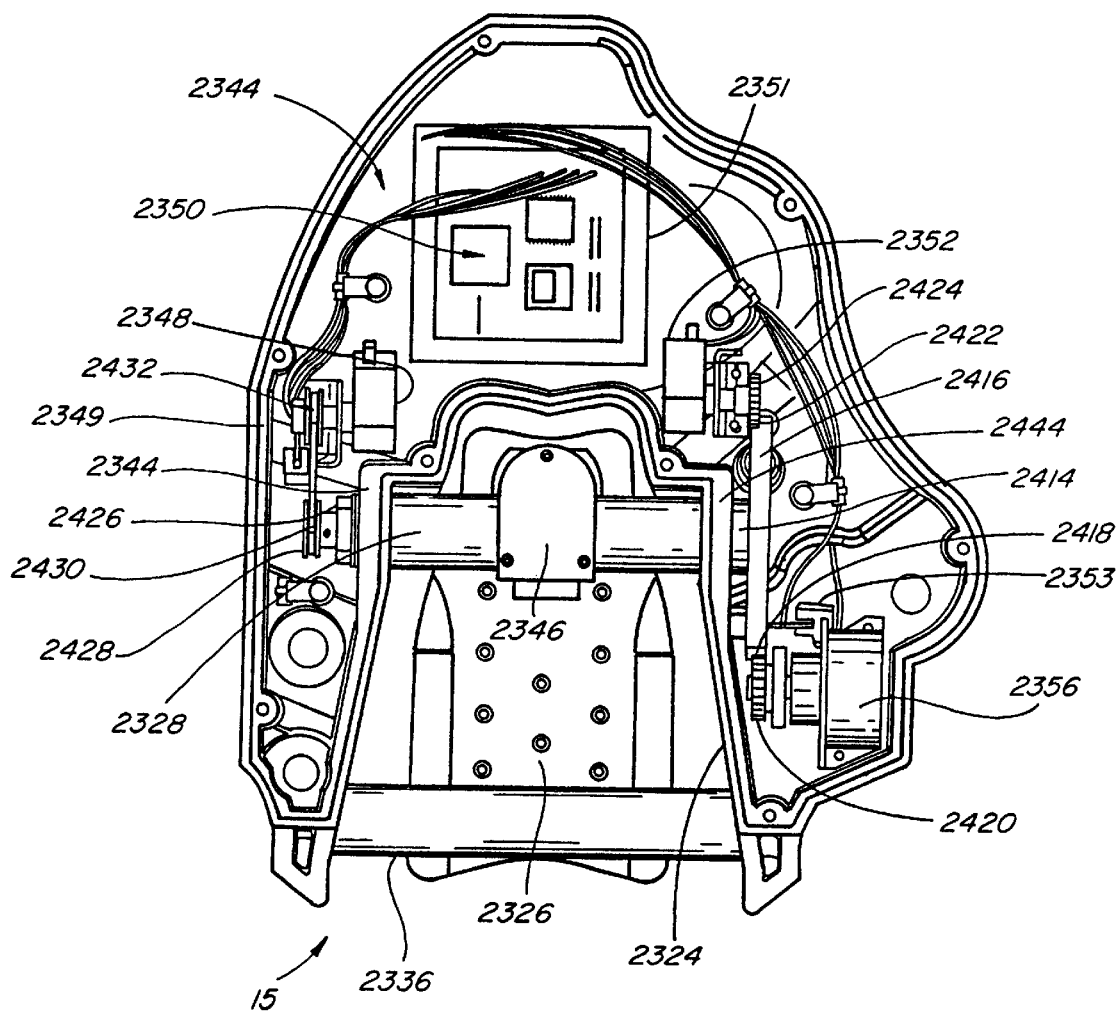
FIG. 3 is a bottom plan view of the foot control, illustrating certain circuit and related components.
Figure 4:
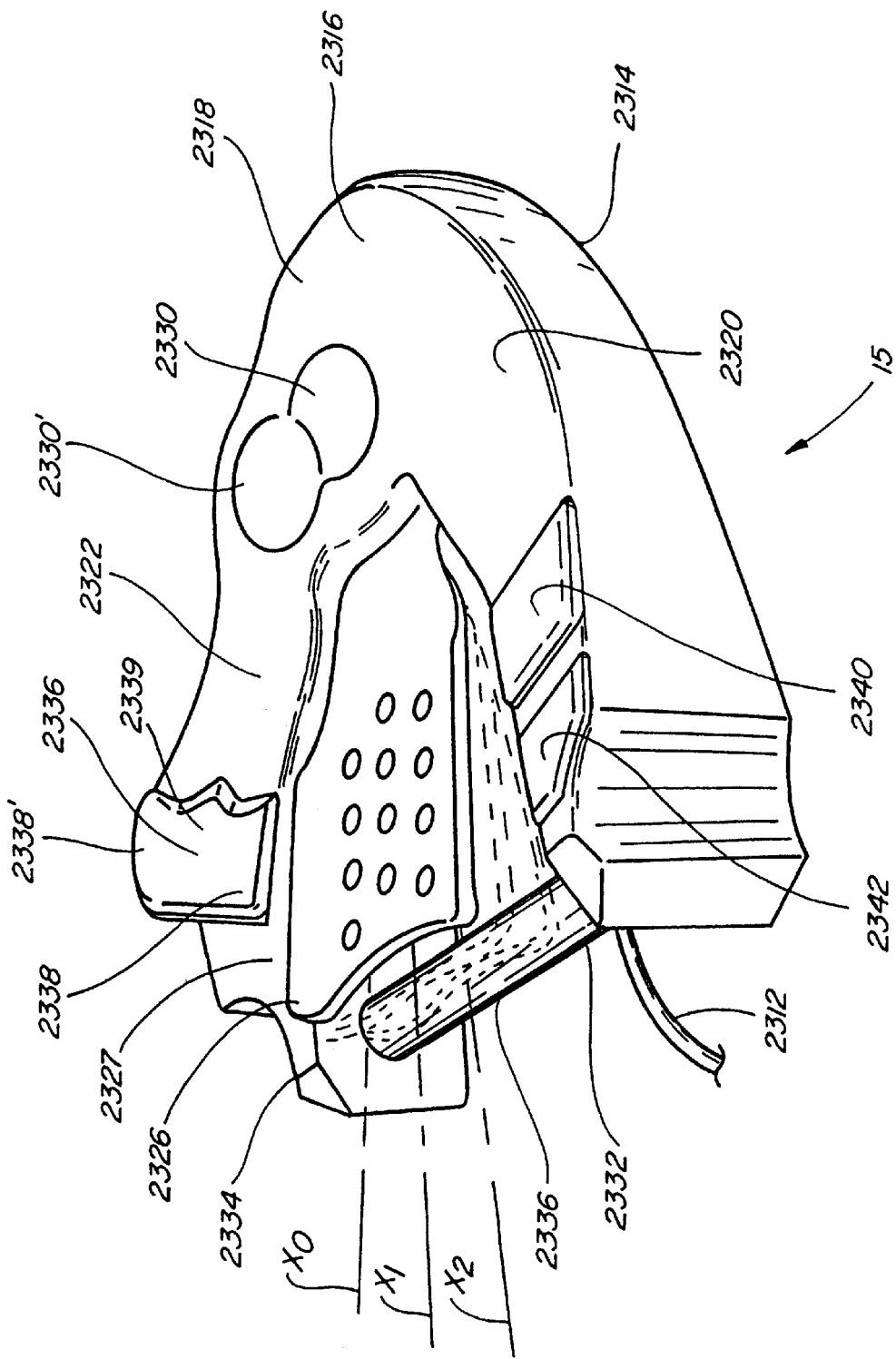
FIG. 4 is perspective view of the foot control.

Referring now to FIG. 3, housing 2314 is shown from the bottom but without a cover, which normally maintains sealing of components, which is shown removed to illustrate components within the interior, generally designated 2344, of housing 2314.

Shaft assembly 2328, as extending through interior walls 2344 of the housing includes at its midpoint a gearbox 2346 in which are located components for translating foot pedal yaw into corresponding rotary motion for driving a yaw encoder 2348 interconnected with microprocessor-controlled circuits 2350 on a circuit board 2351. Such circuits communicate by cable 2312, using RS-485 serial data bus protocol, with the modular microsurgical system 1. Similarly a pitch encoder 2352 is also interconnected with circuit board 2350, and this encoder is driven from the other end of shaft assembly 2328 by one end of a rockable pinion-drive arm 2354 which rocks with pitch movement of the foot pedal, and the features and operation of which arm will be explained below. The opposite end of arm 2354 is interconnected with a magnetic particle brake 2356 which provides electronically-controlled detenting of the foot pedal in its pitch mode, as more fully later described. Associated with yaw encoder 2348 is a limit switch, i.e., home switch, 2349, which serves to illustrate a similar limit switch, i.e., home switch, 2353 (see FIG. 3) associated with pitch encoder 2352.

The yaw and pitch limit switches are connected to circuit board 2350 for signalling home positions of the respective encoders for corresponding home positions of the foot pedal, i.e., when centered (0° yaw) and when not depressed in pitch.

General Circuit Features

Referring now to FIG. 5, a block diagram shows the preferred embodiment of control circuitry 2350 of the new foot control, illustrating its key circuit features. Cable 2312 provides d.c. power at 24 volts to the foot control and a twisted-pair serial bus connection for transfer of data by RS-485 protocol with the modular surgical system.

A power input circuit 2355 provides the voltage supply to a power supply 2356 serving as a Vcc generator for logic circuitry, which provides regulated Vcc low voltage, e.g., 5 v.d.c, to other circuits, including an RS-485 communication transceiver 2358 and RS-485 reset transceiver which both communicate with the serial bus connection-provided by cable 2312. Vcc generator 2356 also serves as the Vcc power source for an integrated circuit ("IC") device, namely a distributed communications and control processor (e.g., processor 225) available from Motorola, Inc. and designated by the registered trademark "Neuron" (of Echelon Corp.), and referred to herein for convenience as the Neuron IC. It is designated 2362, and is interconnected with a memory IC 2364 such as preferably 90 ns or faster 64K×8 flash memory devices commercially available under type designation Atmel AT29C257-90.

Vcc generator 2356 also supplies operating voltage to a logic IC 2366, namely electronically programmable logic device (EPLD), as explained below.

Vcc generator also supplies certain circuit components of a brake drive circuit 2368 which drives magnetic particle brake 2356 for electronically-controlled detenting of the foot pedal. Brake drive circuit 2368 for this purpose is also provided with 24-v. power by power input 2355, thus receiving a voltage adequate for driving brake 2356.

Logic IC 2366 used for switch logic input/output expansion purposes and control and for encoder decoding. Thus, IC 2366 provides switch decoding of the respective limit switches as well as the bipolar and mode switches 2340, 2342 and rocker switch 2336, and all of which switches are here simply represented as a group of the various switches 2370 which are decoded by EPLD logic 2366. Thus also, interconnected with EPLD logic IC 2366 are yaw encoder 2348 and pitch encoder 2352 for quadrature decoding/multiplying.

EPLD IC 2366 also provides brake strength encoding, selecting brake strength, and for this purpose interconnected as shown with brake drive circuit 2368 which includes circuit features for selectively energizing and controlling magnetic particle brake 2356.

Specific Circuit Features

Referring the views of FIGS. 6A–6F, a detailed circuit schematic of the foot control circuitry shows details in accordance with the preferred embodiment.

Figures 1, 6A:
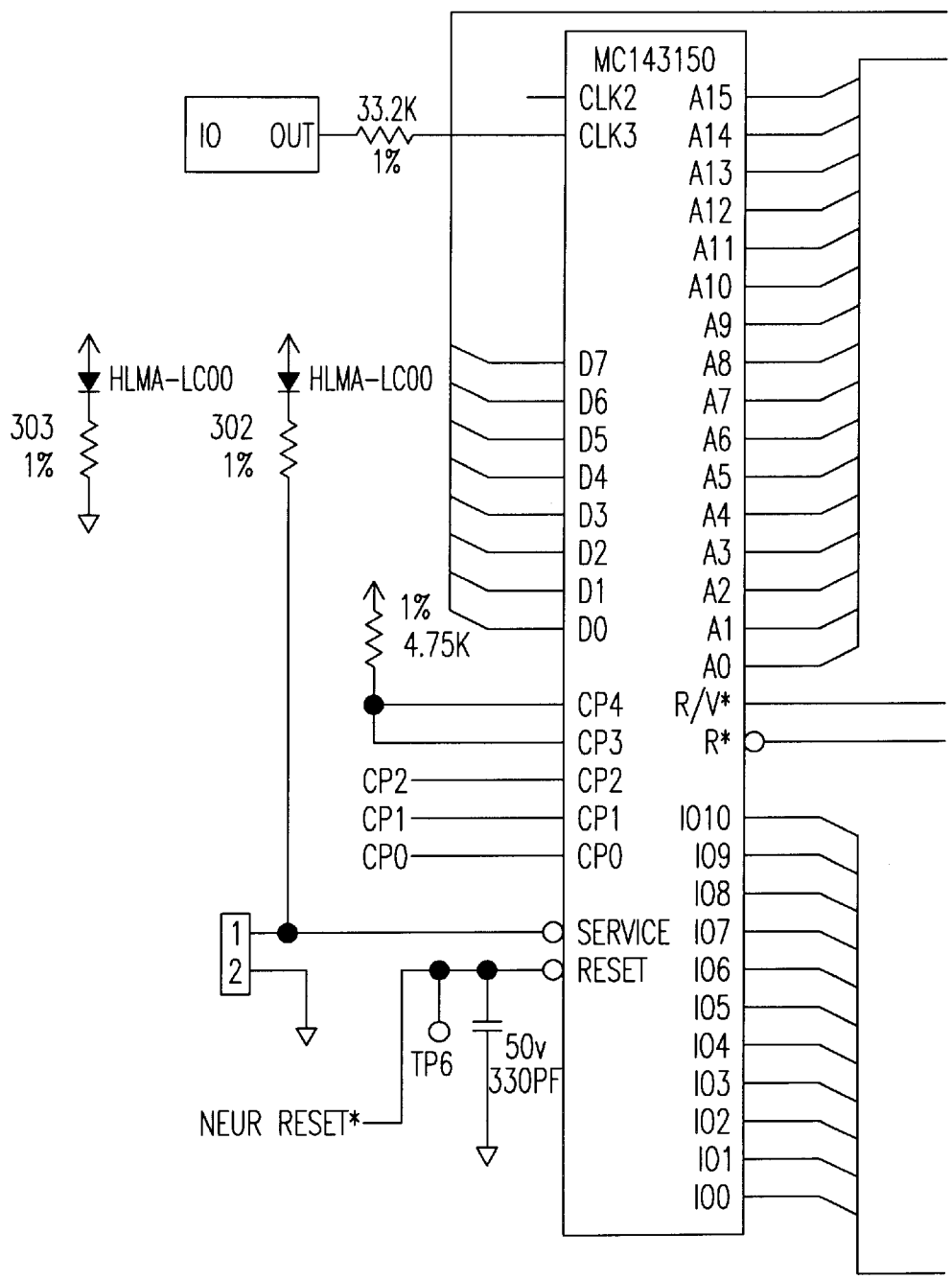
Figures 2, 6A:
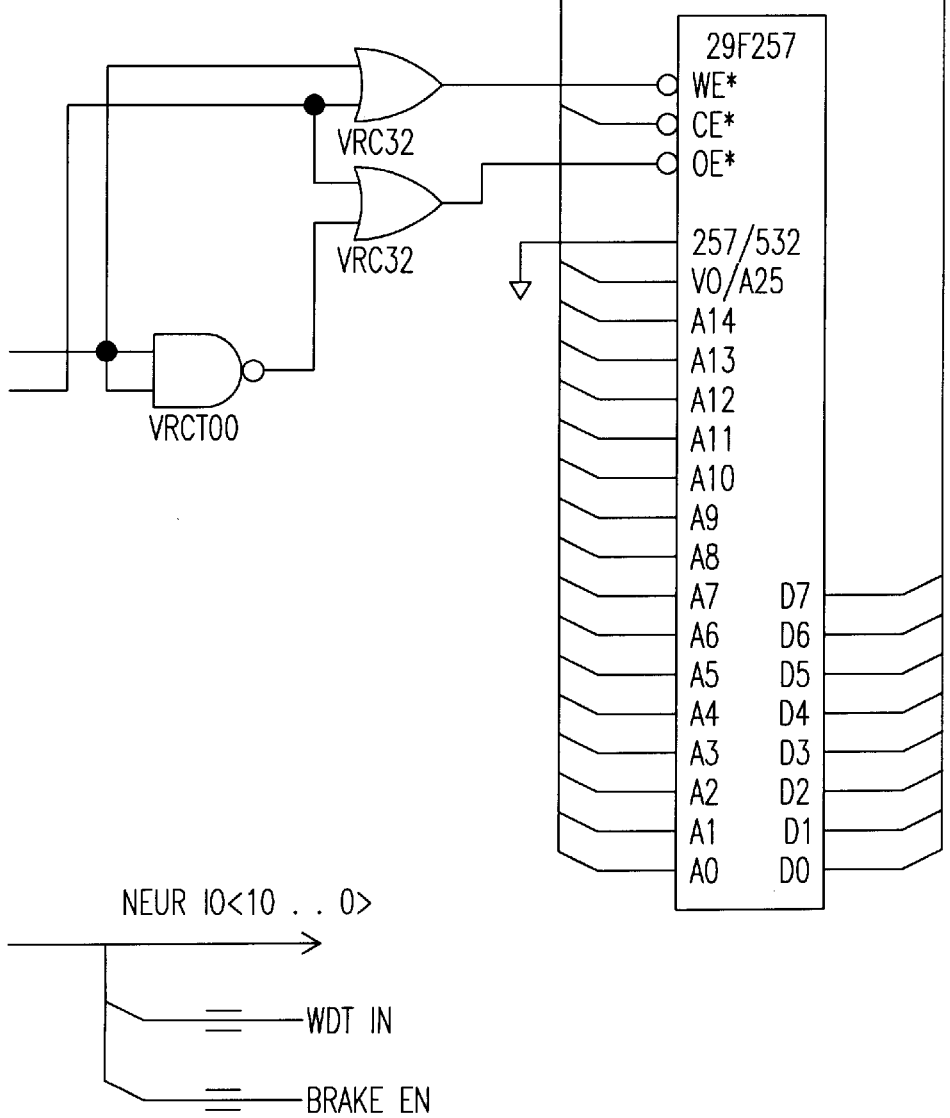

In FIG. 6A, Neuron IC 2362 is provided with a clock crystal input 2372 for its operation and has data and address connections by parallel data transfer with memory IC 2364 in which is stored in resident ROM application program code for Neuron IC 2362. A series of gates 2374*a,b,c* connect IC's 2362 and 2364 and provide signal conditioning for read/write enable control and clocking signals NEUR R/W* and NEUR ECLK, where the asterisk here and elsewhere in the circuitry denotes logic inversion (low true). On-chip RAM internal to Neuron IC 2364 stores data in accordance with the IC 2362 program code.

Figures 1, 6B:
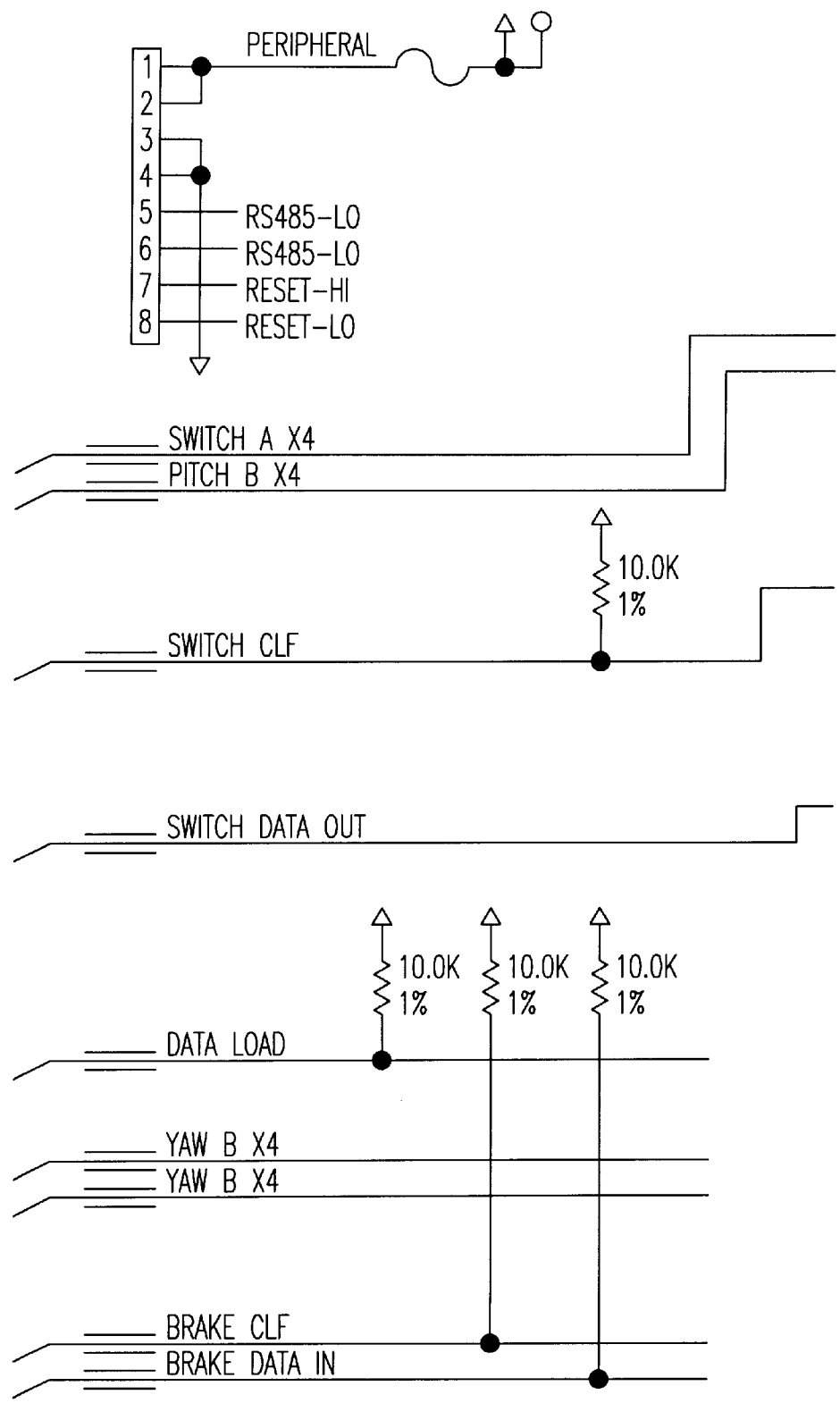
Figures 2, 6B:
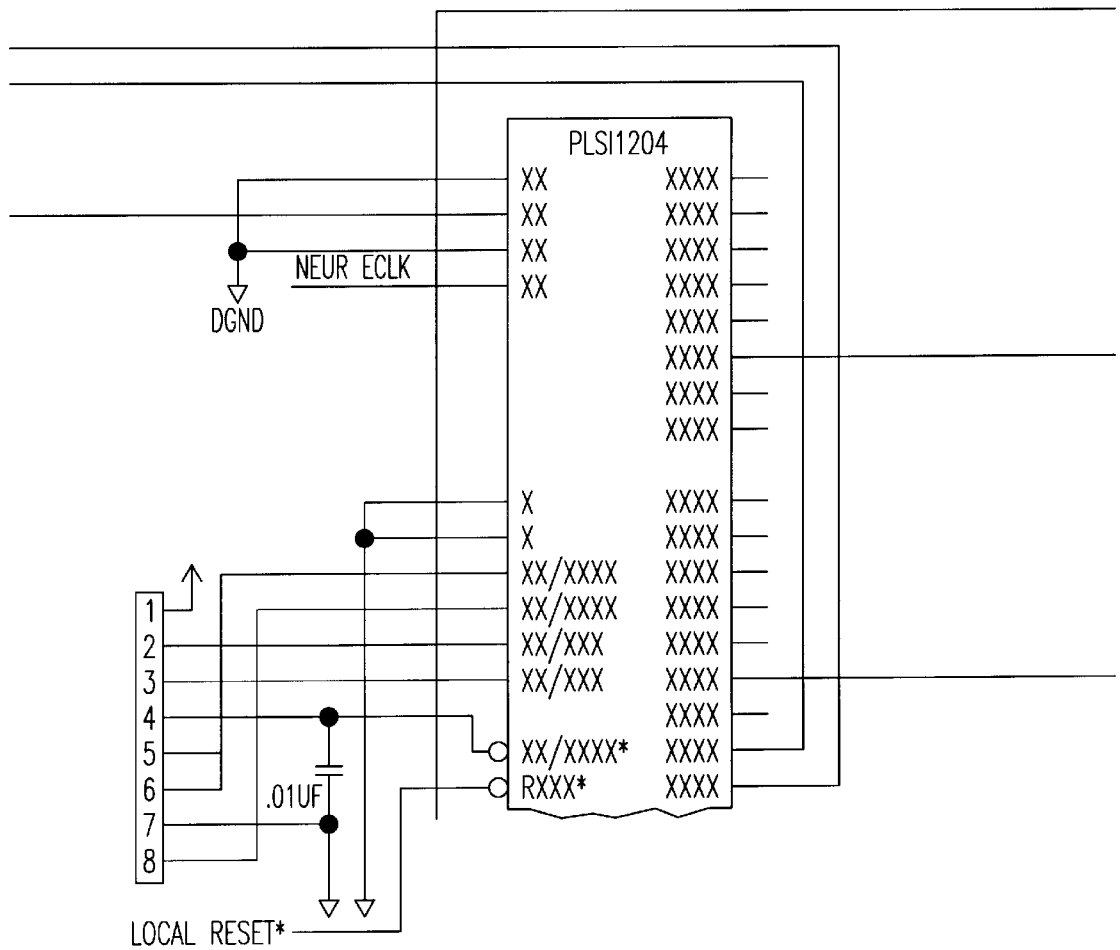
Figures 3, 6B:
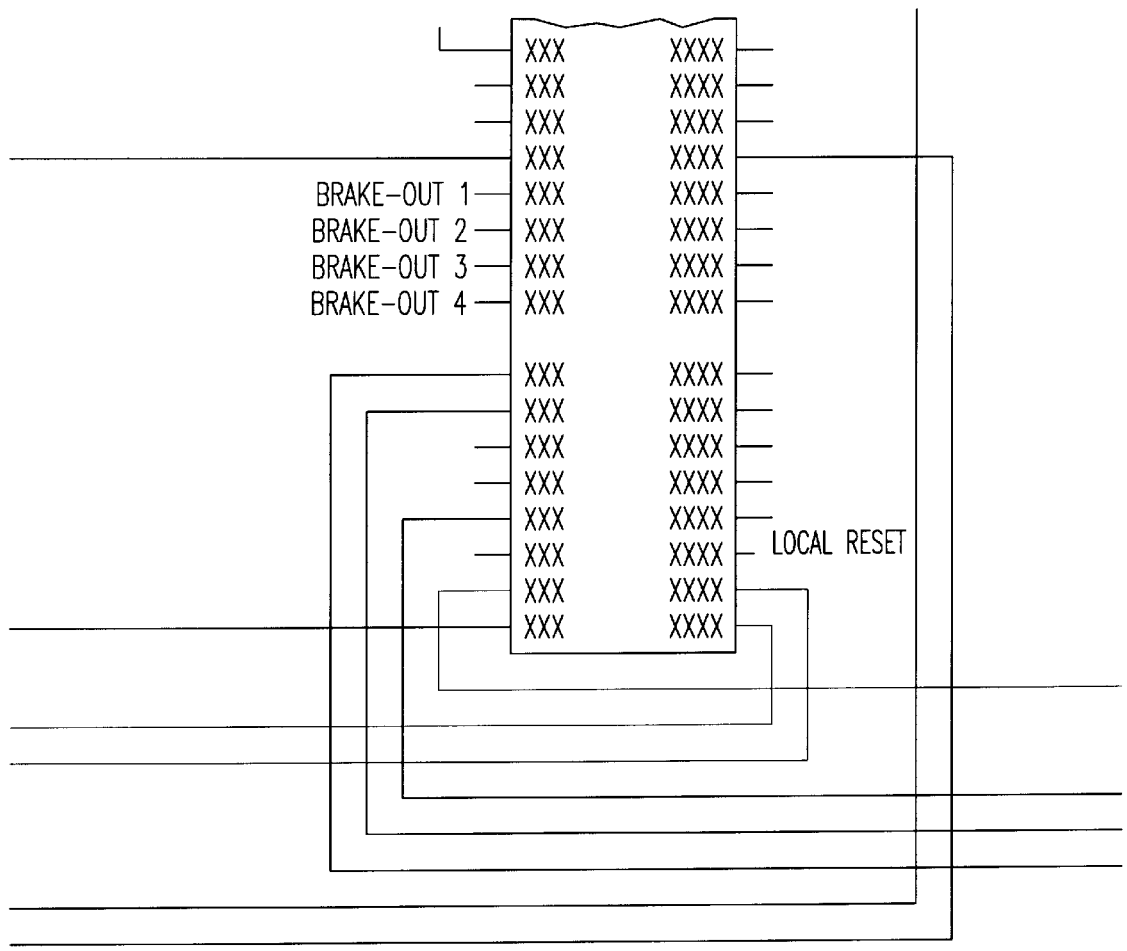
Figures 4, 6B:
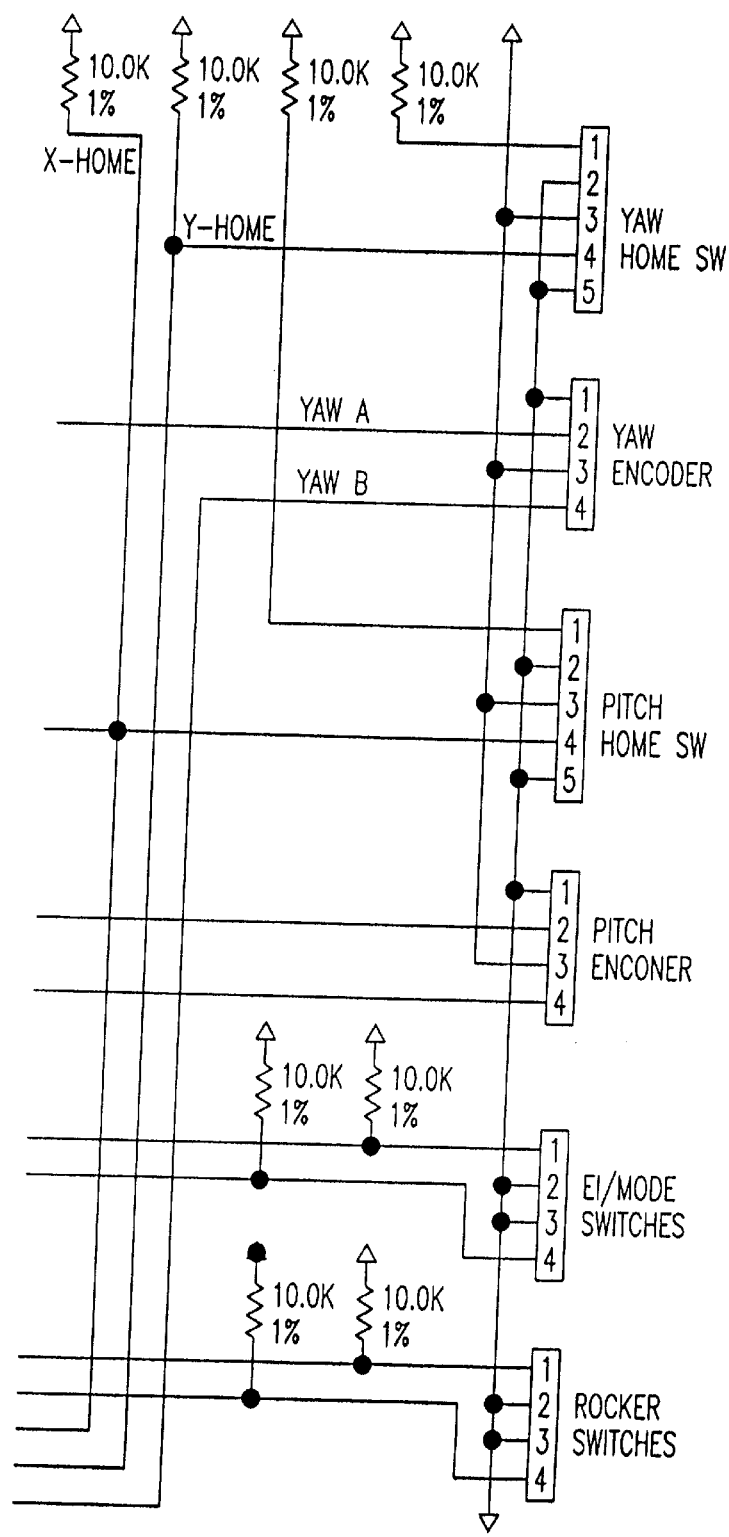

Referring to FIG. 6B, the EPLD IC 2366 is preferably chip device available under Lattice part designation ISP1024. It is provided with inputs by various jacks J10, J5, J8, J3 by which interconnection is made with the various switches generally grouped at reference number 2370 in FIG. 5, discussed hereinabove. It is also provided with inputs by jacks J6 and J9 by which interconnection is made with the encoders for measuring pitch and yaw movement. At the opposite side, a jack J2 shows the main connection of the circuitry by means of cable 2312. EPLD IC 2366 is also interconnected with Neuron IC 2362 input/output terminals by the connection labeled NEUR IO<10 . . . 0> for providing input and output, e.g., the status of the foregoing group, i.e., a matrix, 2370 of switches, and for reporting the yaw and pitch encoder data; and receives the Neuron IC clock signal NEUR ECLK. For reset purposes, EPLD IC 2364 receives reset signals LOCAL RESET and LOCAL RESET* from a reset circuit shown in FIG. 6C.

Figure 6C:
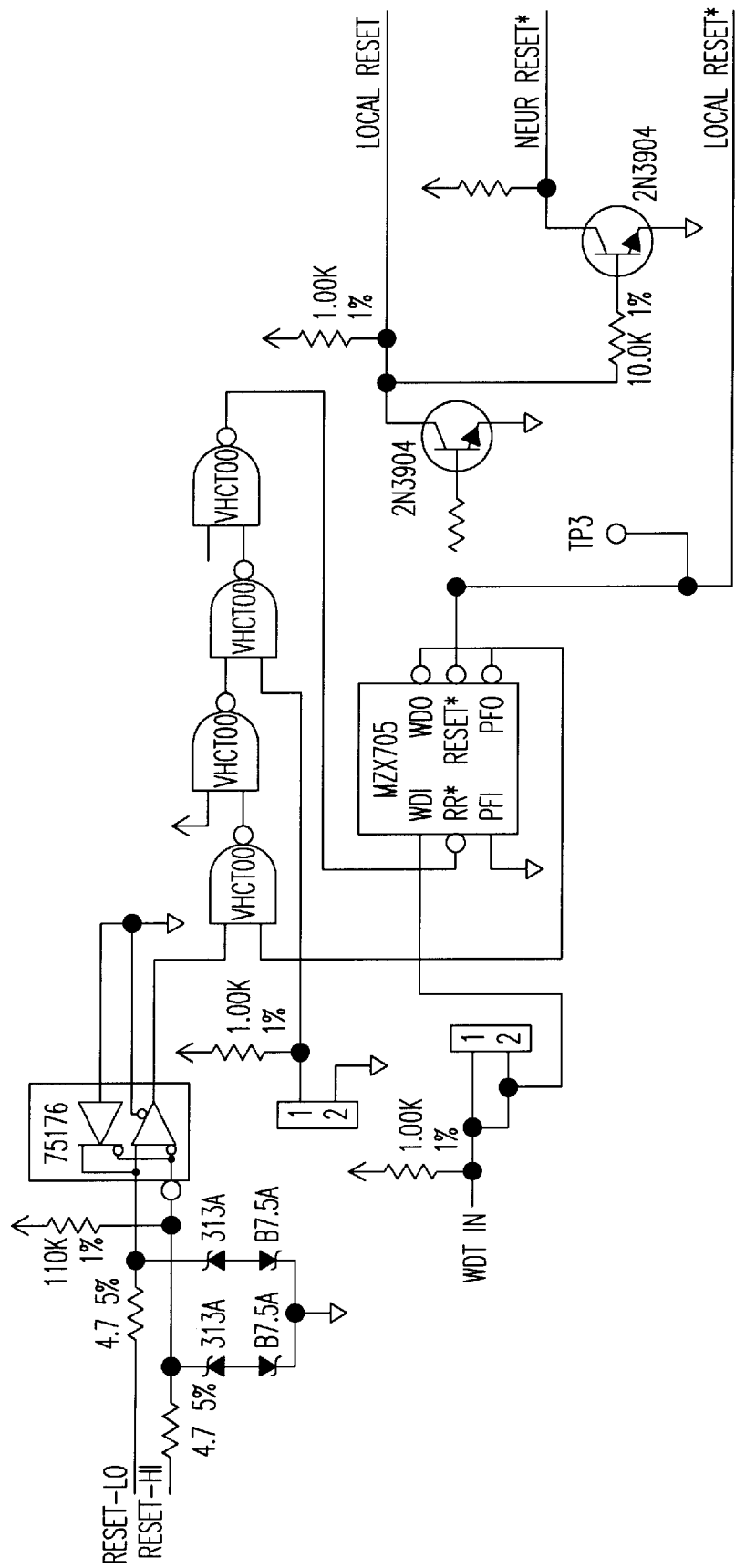

Referring to FIG. 6C, which shows reset circuitry including watchdog timer reset functions, transceiver 2360 is preferably commercial device type 75176, a line-driver/buffer which provides appropriate signal conditioning of reset signals RESET-LO and RESET-HI. A group of logic devices 2376*a,b,c,d* provides conditioning of the signal output of transceiver 2360 to a reset chip 2378, preferably commercial device type MAX705. It is a buffer which receives periodic watchdog timer pulses normally as a signal WDT IN from the Neuron IC 2362. If reset chip 2378 does not receive such a normal watchdog time pulse within the normal pulse interval, it times out to send a reset signal via gates 2376*a,b,c,d* for local resetting the foot control circuitry, providing by means of transistors 2380*a*, 2380*b* three reset signals, LOCAL RESET, LOCAL RESET* and NEUR RESET*. The watchdog timer generates appropriate reset signals within the foot control if a problem occurs within the foot control circuitry, and preferably so resetting at least once every 1.0 sec, the watchdog reset pulse being preferably greater than 50 nsec.

Figure 6D:
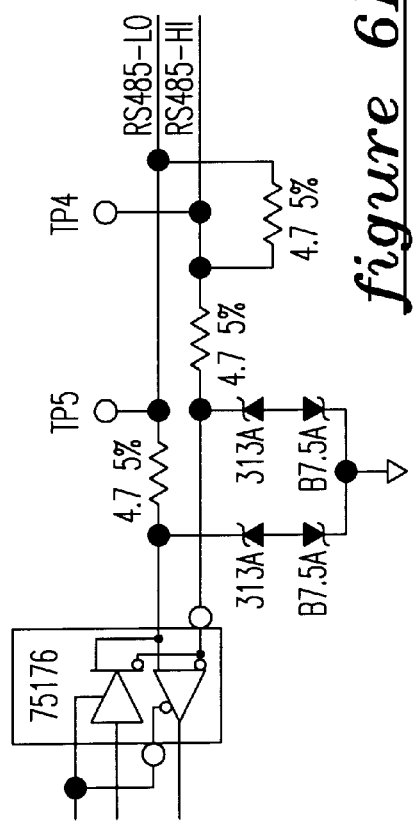

Similarly, FIG. 6D shows communication transceiver 2358 (also referred to as transceiver 223) which is preferably commercial device type 75176. It a line-driver/buffer which provides appropriate signal conditioning for communication signals RS485-LO and RS485-HI as an interface with corresponding local signals CP2, CP1 and CP0 which are the communication protocol signals for Neuron IC 2362.

Diode clamp circuits 2382*a*, 2382*b* are provided respectively for the circuitry of FIGS. 6C and 6D for controlling line levels appropriately for the reset and RS485 signals.

Figure 6E:
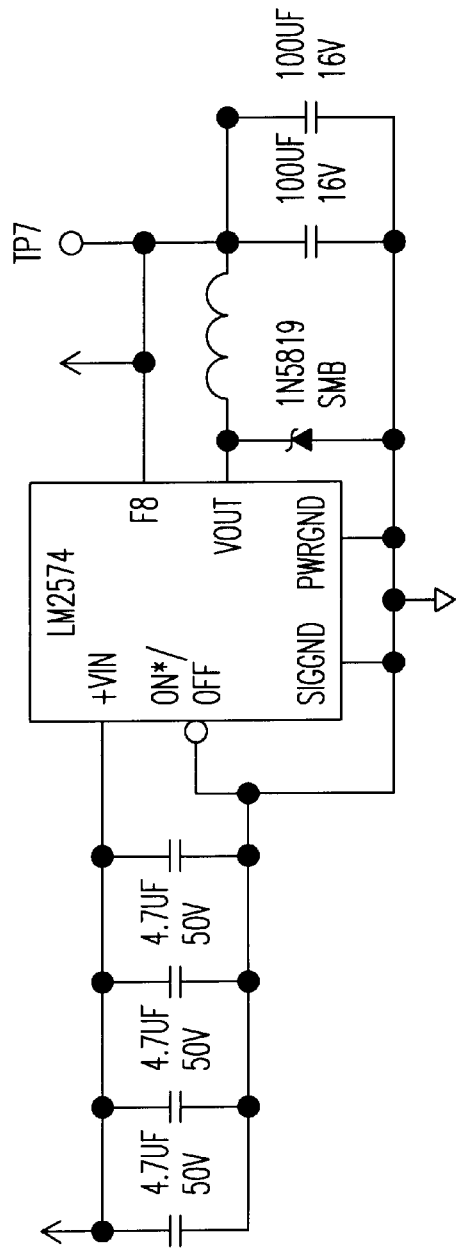

FIG. 6E shows power supply circuitry including commercial chip device LM2574, serving thus as Vcc generator 2356 of FIG. 5, and its circuit design will be understood by those skilled in the art and is generally derived from application notes as provided by National Semiconductor, Inc.

Foot Pedal Detent Brake Drive Circuit Features

Figure 6F:
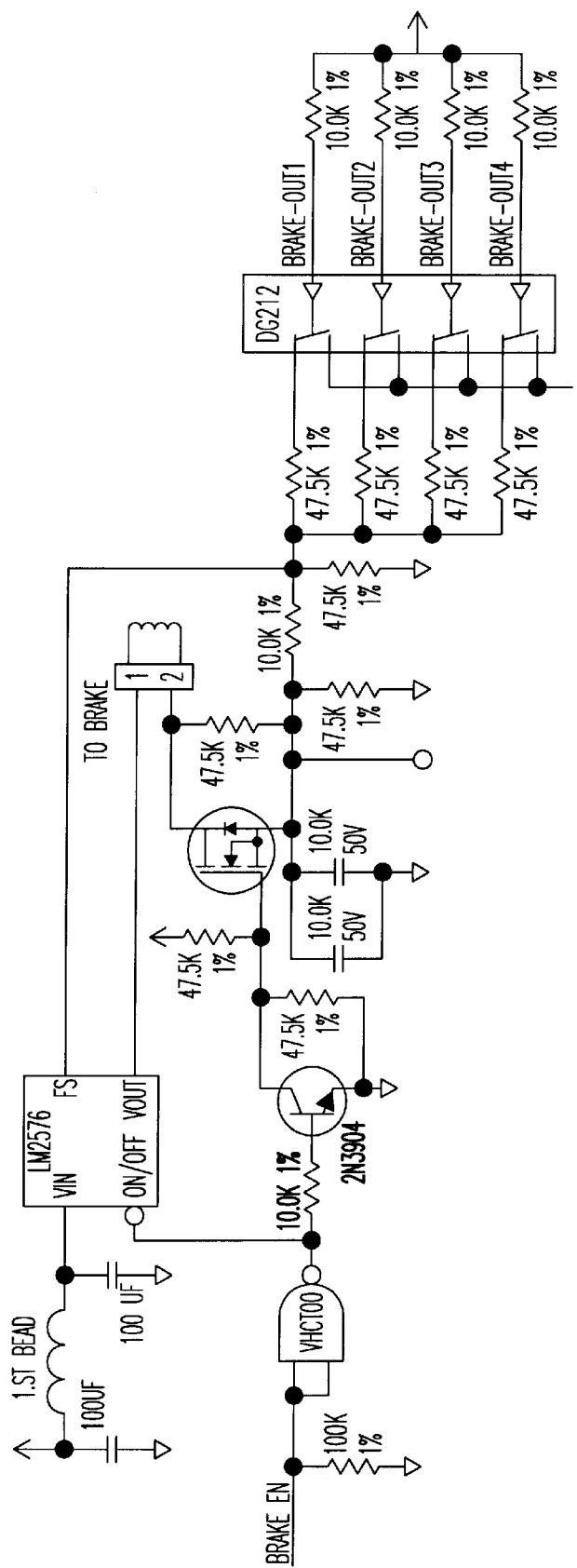

Referring to FIG. 6F, brake drive circuit 2368 (FIG. 5) is shown in specific detail.

Figure 7:
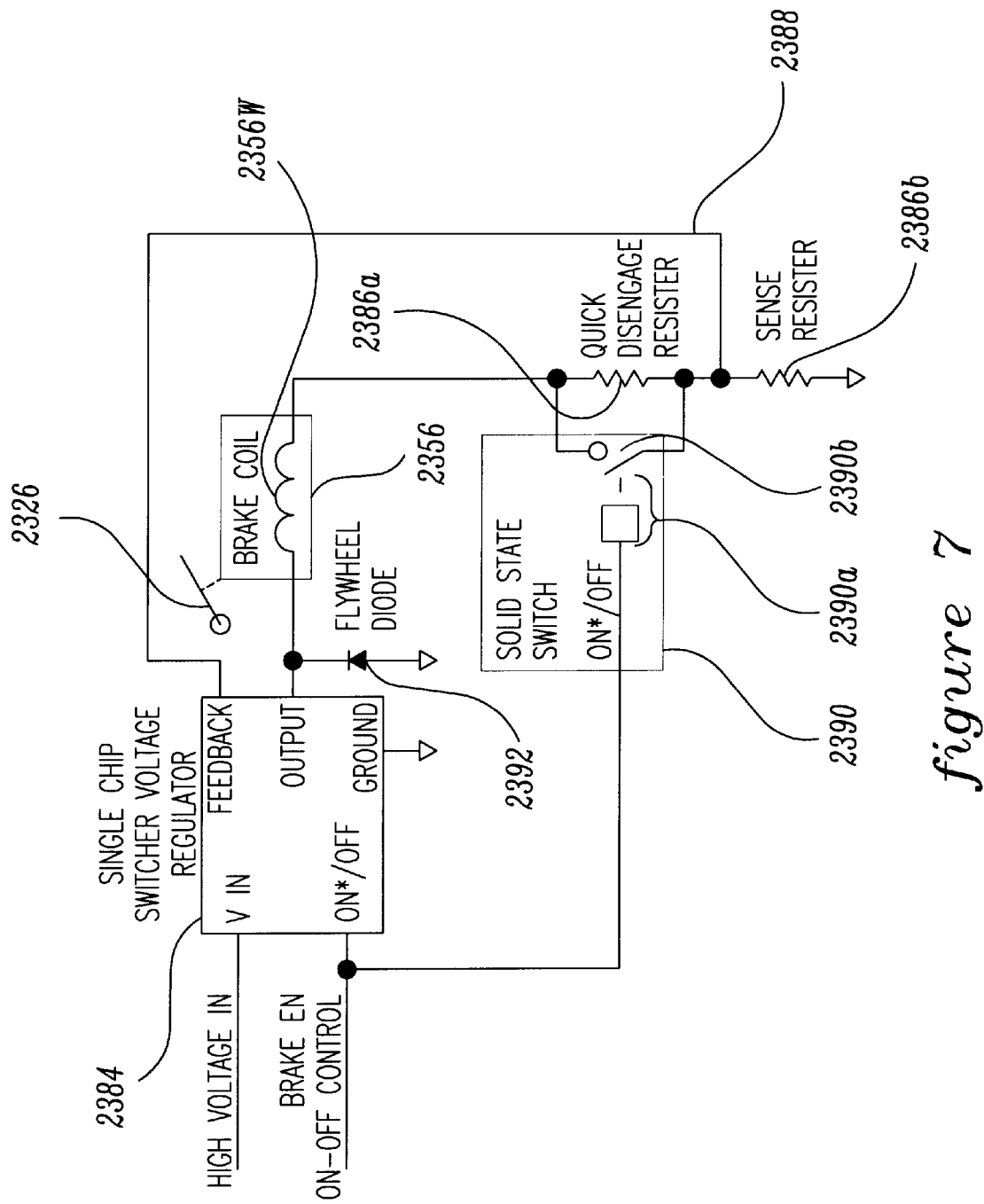
FIG. 7 is a block circuit diagram of the brake drive circuitry.

Prior to considering FIG. 6F, attention is directed to FIG. 7, a block diagram of the brake control circuitry, which shows the input of a brake enable signal BRAKE EN to be received by this circuitry for enabling driving of magnetic particle brake 2356 by which detenting of foot pedal 2326 is achieved.

As will be appreciated the coil 2356W (FIG. 6F) of magnetic particle brake 2356 has a high inductance which slows its response time to engage and disengage. Thus, the brake control circuitry will provide means for speeding up this response time upon braking by first energizing the brake coil with a voltage significantly higher than its normal operating voltage. Then, once the current in the brake has reached the required operating value, the drive voltage must be reduced to a level to maintain that operating current. One conventional method to achieve a faster response is to apply a fixed high voltage to a ballast resistor in series with the brake coil; but the ballast resistor consumes excess energy and produces unwanted heat.

The present arrangement as shown in FIG. 7 provides for rapid engaging and disengaging of the brake without an excess consumption of power. This is accomplished in part by using a pulse width modulated drive for the brake, the pulse width being feedback voltage-controllable, specifically employing a DC-to-DC switching voltage regulator circuit, namely comprising a switching-type power supply chip device 2384, most preferably a single chip switcher voltage regulator, which operates to provide a constant voltage supply; and specifically provides a constant current through the brake coil, which constitutes a highly inductive element in the switching voltage regulator circuit.

BRAKE EN is here shown as ON-OFF CONTROL signal provided to an ON*/OFF input of chip device 2384, having a V IN input which receives a suitably high voltage (24 v.d.c.), being thus high enough for efficiently driving the coil winding 2356W of magnetic particle brake 2356 which when energized exerts drag on the mechanism of foot pedal 2326, here shown by dotted line connection (connecting foot pedal 2326 and brake 2356) to create a detent feedback by establishing a selectively variable force resistance to further pushing of foot pedal 2325, as well as modulating such force resistance in accordance with the operation of Neuron IC 2362 so that the user may have the feeling of pushing through a detent position, so as to in order readily to perceive the point of transition from one region to the next.

Chip voltage regulator, being a switching-type power supply, provides at a terminal OUTPUT a switched output (e.g., at 52 kHz) for constant energization of a circuit including the coil winding 2356W, a quick disengage resistor 2386*a* and a sense resistor 2386*b*, which develops a voltage which is proportion to the current in coil winding 2356W. These two resistors provide a node 2387 between them for a feedback connection 2388 provided to a FEEDBACK input of chip device 2384, so as to control the duty cycle of device 2384, and so modulating its output voltage to maintain the required operating current in brake coil winding 2356W and resistances 2386*a* and 2386*b*.

A solid state switch 2390 includes an electronic switching element with contacts 2390*b* are connected to bridge across and short resistor 2386*a* when enabled by the brake enable signal BRAKE EN which is made available to ON/OFF*.

In this regard, resistor 2386*a* acts as a quick disengage resistor, for it is shorted by operation of contacts 2390*b*, and resistor 2386*b* acts as a sensing resistor, as the voltage across it defines the feedback signal provided by feedback connection 2388 for controlling the brake current. A flywheel diode 2392 completes the circuit.

If then a brake enable signal BRAKE EN appears, the switching power supply chip 2384 is turned on and the solid state switch 2390 operates with speed typical of semiconductor switching devices, bypassing the quick disengage resistor 2386*a*. PATENT Thus the sensing resistor 2386*b* develops a voltage providing pulse width modulation feedback control signal to the switching power supply to control current in the loop including brake coil winding 2356W, and the FET serves as solid state switching means for rapidly increasing loop current for brake actuation by initially providing to the brake coil winding 2356W a brake drive voltage significantly higher than its normal operating voltage, and when the brake current has reached a required operating value for braking action, the brake drive voltage being reduced to a level to maintain an operating current for braking action.

Then, should the BRAKE EN signal disappear, switching power supply chip 2384 is turned off solid state switch 2390 again deenergizes with speed typical of semiconductor circuits, removing the current bypass the FET provides, and thus with extreme rapidity diverts current flow through quick disengage resistor 2386*a*, causing the loop current through brake coil 2356W to drop quickly, and this will immediately be sensed by the user as the passage of the detent. In this way the user is tactilely signalled that the foot pedal has pushed through the detent position, and receives a palpable sensation of transitioning from one activation region of the foot pedal to another.

The circuitry enables more than one detent position, and enables the magnitude of the magnetic particle brake-induced detent to be preset according to predetermined criteria, which may include preference of the surgeon-user, e.g., as for higher resistance or lower resistance detent. It further enables the regions of activation of the foot pedal to be selectively varied in arcuate extent.

Referring to FIG. 6F, the preferred circuit actualization of the circuitry of FIG. 7 is illustrated.

The brake enable signal BRAKE EN is provided through a logic gate 2393 for being sent with inversion (low true) to an inverting input of chip regulator 2384, which receives its 24 v.d.c. power through an inductive-capacitive filter 2394.

The inverted output of gate 2393 drives the base of a transistor 2396 which, as will be apparent, is connected to control accordingly the state of solid state switch 2390, here seen to be constituted by an FET having an internal reverse polarity transient clamp diode 2391 connected across the drain and source electrodes which effectively provide the contacts 2390*b* shown in FIG. 23*5*, and across which is connected disengage resistor 2386*a*. Sense resistor 86*b* is supplemented by a resistor divider pair 2398*a*, 2398*b* between which is a node 2399 to which four resistors 2400*a,b,c,d* are connected at one end and at their opposite ends to corresponding switching outputs 2402*a,b,c,d* of a solid state switching device 2402 which preferably is commercially available chip device type DG212, which will be understood to selectively connect any one of resistors 2400*a,b,c,d* to ground dependent upon the presence or absence (high or low) of brake intensity control signals BRAKE-OUT1, BRAKE-OUT2, BRAKE-OUT3 or BRAKE-OUT4 at corresponding inputs of switching device 2402, and which inputs are biased to Vcc by corresponding resistors 2404*a,b,c,d*. From the foregoing it will appear that resistors 2402*a,b,c,d* together act with resistor 2388*b* to provide a voltage divider for altering the voltage level at node 2387 in a sense for controlling the feedback 2388 so as to predetermine the extent to which brake winding 2356W will be energized when FET 2390 switches to its conductive state, and dependent upon brake intensity control signals BRAKE-OUT1, BRAKE-OUT2, BRAKE-OUT3 or BRAKE-OUT4 provided by Neuron IC 2362 in accordance with program selection by the modular microsurgical system, so that each of such brake intensity control signals defines a braking detent value from minimum to maximum.

Referring to FIGS. 8A, 8B and 8C, the operation of the control circuitry of the foot control will now be more clearly understood.

Neuron IC 2362 software operates in an idle loop until an event occurs. An event would be operating one of the push buttons of group 2370, change in yaw encoder 2348 or change in pitch encoder 2352.

FIG. 8A illustrates Neuron IC-defined push button sequence. Neuron IC 2362 effectively establishes by its software a push button timer interval during which the pressing of any of the footswitches may be detected. A first step 2406-1 shows expiration of the push button interval. During a second step 2406-2, serial data input may be received by Neuron IC 2362 from the microsurgical system. A next step 2406-3 checks to see if any of the home switches, i.e., those associated with yaw encoder 2348 or pitch encoder 2352 are engaged, i.e., indicating that the foot pedal is neither depressed nor yawed. If so ("Y" for yes), the encoder counts are zeroed at step 2406-3A. If not ("N" for no), step 2406-4 represents a check to see if new buttons are pressed. If so ("Y"), the condition is reported at step 2406-5 via the network connection cable 2312 to the modular microsurgical system processor. If not ("N"}, the event cycle is done, shown by step 2406-6; and the idle loop continues similarly until an event occurs.

As shown in FIG. 8B, if there is yaw encoder 2348 change, a step 2408-1 represents its detection. In step 2408-2 the new position limit is detected. The data is then sent to the system processor at step 2408-3.

As shown in FIG. 8C, in the case of pitch encoder 2352 change, a step 2410-1 shows detection of the change. In step 2410-2 the new position limit is computed. Step 2410-3 follows in which detent management is calculated. Thus, at an appropriate encoder limit, brake winding 2356W is energized appropriately for creating detenting of movement of the foot pedal, which is fully as palpable to the user as if there were mechanical devices. The data representing the conditions so measured is sent to the system processor at step 2410-4.

Figure 9A:
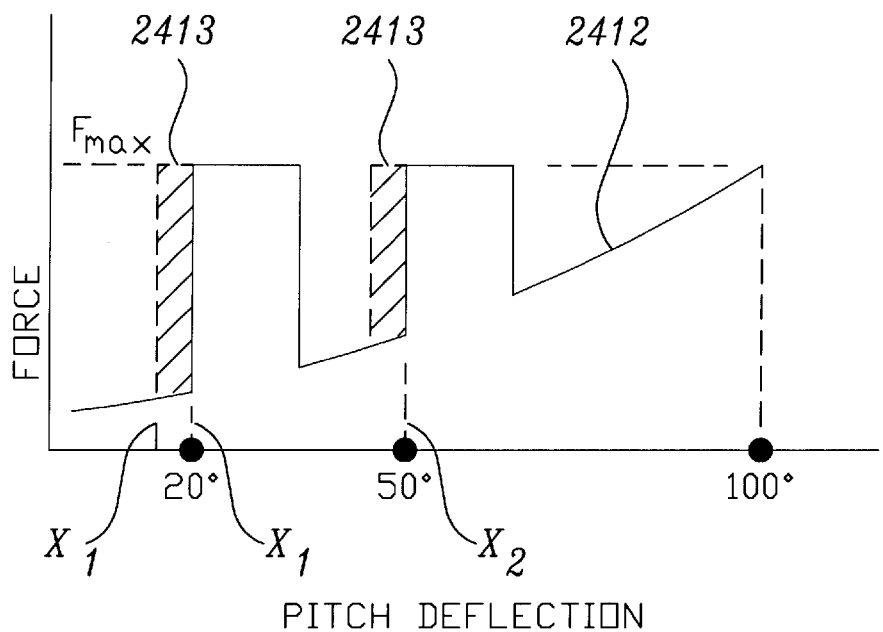
FIGS. 9A and 9B are graphical representations indicating different detent possibilities for operation of the brake drive circuitry.
Figure 9B:
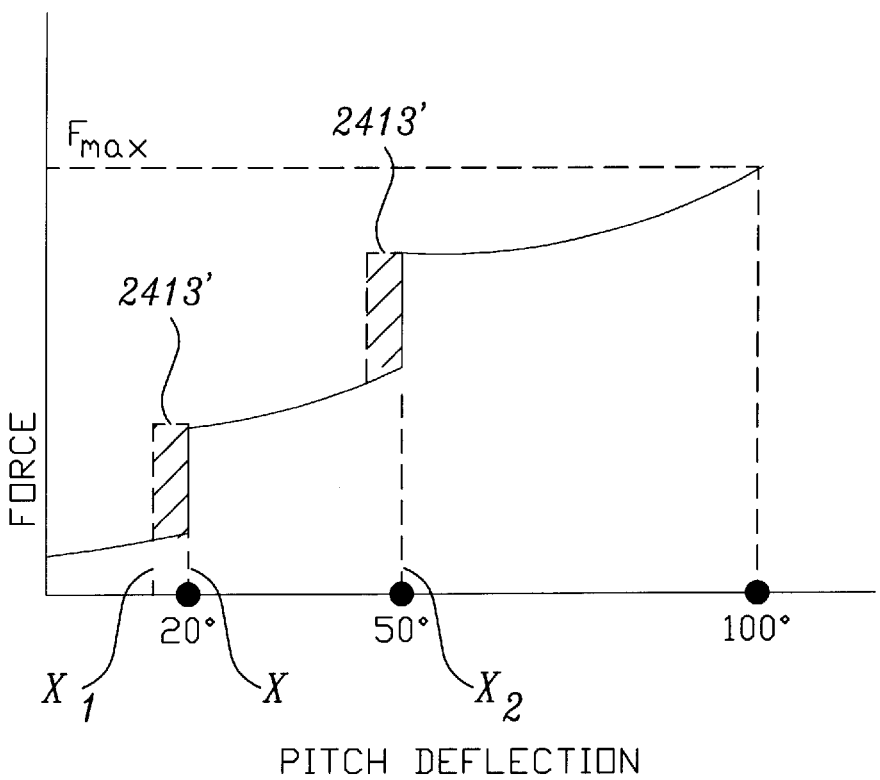

Different detent methods are possible in operating foot pedal 2326 by the brake control and foot pedal control circuitry described. FIGS. 9A and 9B indicate the possibilities. In both, relative braking force is plotted against the percentage of foot pedal deflection in pitch, from 0% through 100%, with detent points being indicated as at $x_1$, $x_2$.

In FIG. 9A, the curve (with dotted extensions) 2412 represents normal $F=kx^2$ pedal force increasing from a low minimum value $F_0$ to a maximum value $F_{max}$. At a deflection of $x_1$, e.g., 20%, breaking force is applied to provide pedal force $F_{max}$ (or a lesser chosen value) is quickly applied as a pulse. Passing through the detent thus created, pedal excursion continues until a second point $x_2$, e.g., 50%, and again breaking force is applied to create pedal force $F_{max}$ (or a lesser chosen value) is quickly applied as a pulse. Preferably, in using this pulse-type method of detenting, hysteresis between brake force on and brake force off is used. As shown in the first pulse of FIG. 9A, $x_1$ shows the point of first energization, $x_1'$ shows a lower value of depression provided during retarding the pedal before the user can turn off the detent, so as to prevent the user from being on an edge point in which the detent would be toggling on and off. Thus a shaded hysteresis area 2413 of the pulse is indicated. A similar hysteresis 2413 is provided also for the next brake pulse initiated at $x_2$.

In a second possible method shown in FIG. 9B, pedal excursion to the first position $x_1$ results in quick application of a braking force to bring pedal force to a value $F_1$. The breaking force is maintained while pedal force continues along a shifted $F=kx^2$ curve until a second point $x_2$, e.g., 50%, and again breaking force is increased quickly to create pedal force $F_2$, from which pedal force may increase along the normal increasing-force curve to its maximum value of $F_{max}$. Hysteresis may in this method also be used to keep the user from being on a foot pedal edge point, as would toggle on and off braking force if the user were to ease the foot pedal back slightly from one of the detent points. A shaded hysteresis band area 2413' of the pulse is indicated, wherein once braking force is engaged at $x_1$ it will not be disengaged until the pedal retracts over a hysteresis interval down to $x_1'$. A similar hysteresis band 2413' is provided also for the next brake increase at $x_2$.

Referring now also to FIG. 3, the detent points $x_1$ and $x_2$ are shown by positions of foot pedal 2326 illustrated in dashed lines. The software permits the detent points $x_1$ and $x_2$ to be varied, as a percentage of foot pedal travel. Thus by use of screen display of the microsurgical system, the user can be enabled if desired to vary the detent points, as well as the extent of braking force signalling the detent points.

Referring now to FIGS. 232, 239 and 240, aspects of the mechanical design by which the foot control is responsive to movement of foot pedal 2326 in pitch and yaw will be appreciated. At 2414 in FIG. 3 is indicated a shaft extension of shaft assembly to which is affixed for rotation with foot pedal 2326 in pitch an actuating arm 2416 having a first set of teeth 2418 at one end for meshing with a pinion 2420 carried by the shaft of magnetic particle brake 2456 and a second set of teeth 2422 at the other end for meshing with a pinion 2424 carried by the shaft of pitch encoder 2352. Home switch 53 which determines the home limit of pitch encoder 2352 is not collocated with it, but is instead proximate brake 2356.

At the opposite end of shaft assembly, with its gearbox 2346, is a yaw shaft extension 2426 carrying a pulley 2428 about which is a belt 2430 extending around a corresponding pulley 2432 carried by the shaft of yaw encoder 2348.

Figure 10:
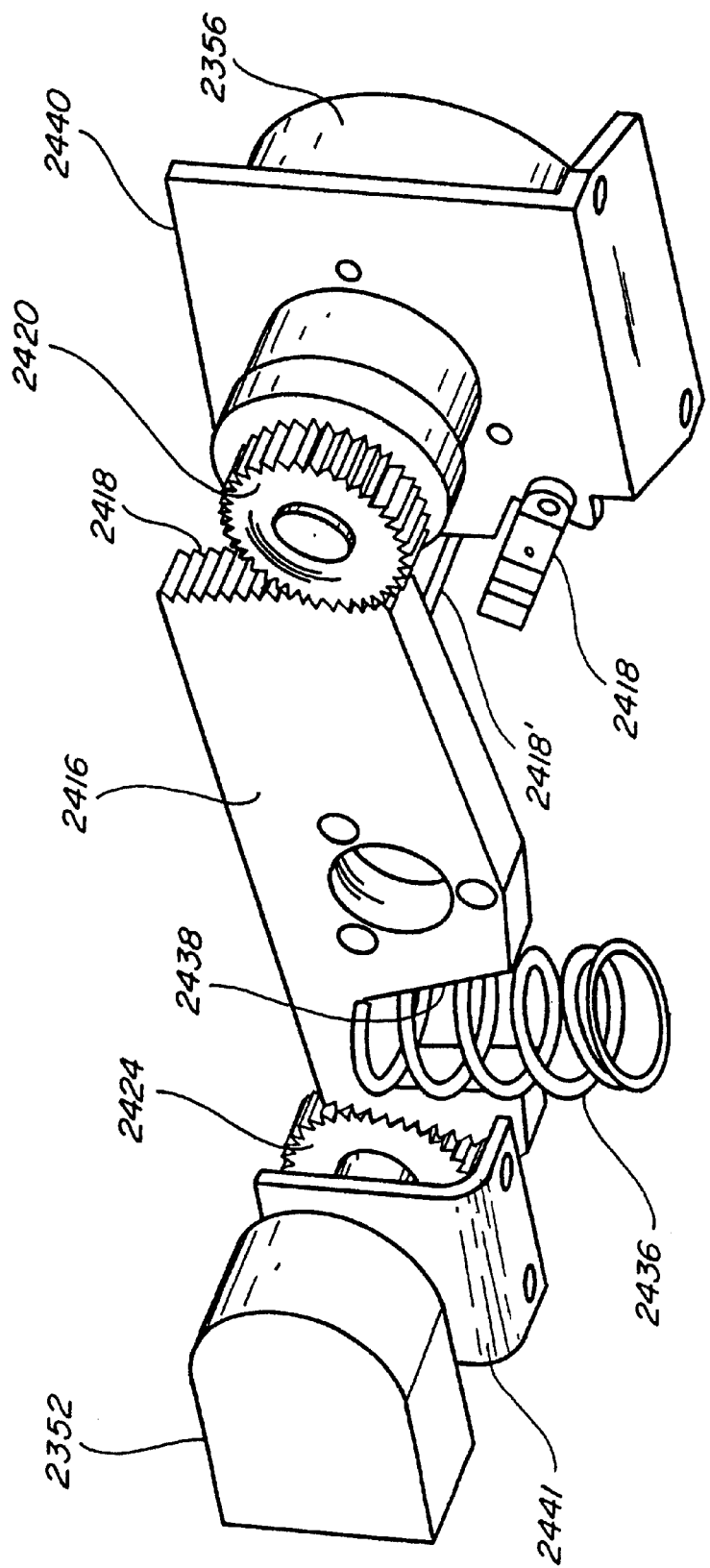
FIG. 10 is a perspective view of certain pedal mechanical features, illustrating brake pedal pitch-responsive components.

As shown in FIG. 10, considered with FIG. 3, actuating arm 2416 meshes at its opposite ends with encoder pinion 2424 and brake pinion 2420, being rockable about the axis of a bore 2434 (to which shaft extension 114, here removed for illustration clarity) is secured for rotation about such axis as the foot pedal is moved in pitch. A coiled compression spring 2436 seated within a recess 2438 of arm 2416, and bearing at its outer end against suitable structure of housing 2314, urges arm 2416 in a clockwise sense as viewed in FIG. 10, for biasing brakepedal 2326 to home pitch position (i.e., which it will occupy when not pressed by the user). Home switch 2418 is actuated when in the home position by an actuator arm 2418', carried by arm 2416 proximate teeth 2418, is sensed by components of switch 2418, as by electro-optical sensing. A bracket 2440 affixes brake 56 within foot pedal housing 2314. A bracket 2441 is provided for similarly affixing pitch encoder 2352.

Figure 11:
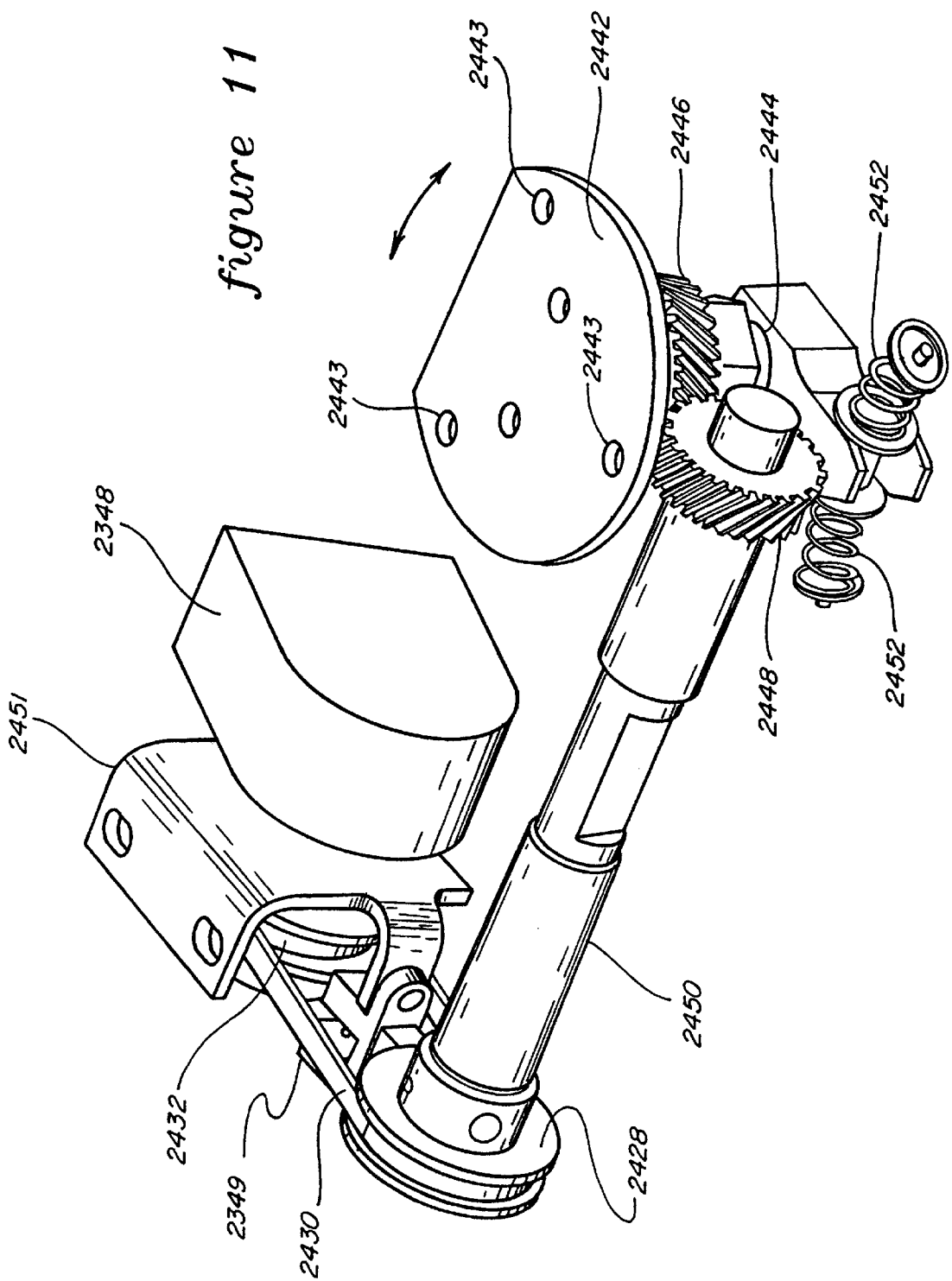
FIG. 11 is a perspective view of certain pedal mechanical features, and illustrating brake pedal yaw-responsive components.

Referring now also to FIG. 11, and with comparison to FIG. 3, gearbox housing 2346 and shaft assembly 2328 (both evident in FIG. 3) are stripped away in FIG. 11 to reveal elements more clearly. Within gearbox housing 2346 is a gear assembly driven by a plate 2442 for securement to foot pedal 2326 by suitable screw affixation through apertures as at 2443. Extending below plate 2442 is a shaft 2444 which carries a helical gear 2446 which meshes with a corresponding gear 2448 affixed to a yaw coupling shaft 2450 which carries at its outer end pulley 2428. It will be evident that yaw of plate 2442 in response to user positioning of foot pedal 2326 in yaw will rotate drive gear 2446 for causing corresponding rotation of shaft 2450 and pulley 2428 affixed thereto, and such rotation will be coupled by belt 2430 to pulley 2432 of yaw encoder 2348, which is affixed to the foot control housing by a suitable bracket 2451. Limit switch 2349, which detects the home position (corresponding to 0° yaw) may be of the same optoelectronic type as pitch home switch 118. A pedal-centered 0°-yaw position of plate 2442 is maintained by the centering action of a pair of coiled compression springs 2452 affixed centrally to an arm 2454 carried by the lower end of shaft 2444, as the outer the outer ends of springs 2452 bear against appropriate seats within gear housing 2346 (FIG. 3).

It is accordingly seen that shaft assembly 2328 provides independent shaft coupling of the separate possible pitch and yaw movements by providing separate shaft outputs at the opposite ends of the shaft assembly, respectively operating the yaw and pitch encoders 2348, 2352 independently and permitting their location relatively remote from shaft assembly 2328, and without requiring them to be difficultly incorporated into the actual foot pedal pivot or mounting mechanism, and thereby providing a more convenient arrangement for assembly and adjustment, as well as achieving an efficient, highly reliable construction capable of withstanding the substantial rigors of surgical use year after year in the operating room environment.

Specific Operational Features

Operation of the new foot control provides hitherto-unavailable flexibility in meeting each user's preferences, as well as ability to change parameters associated with such preferences during use. When employed in the microsurgical system, the new foot control provides the primary input for a surgeon to interact with the system, allowing both linear inputs by either left-footed or right-footed actuation of foot pedal 2326 in pitch and yaw, and provides also push-button actuated binary control. The foot control also affords the surgeon complete control over what function is assigned to what linear control or what button. Through symmetrical placement on foot control housing 2314 of the linear controls and push buttons described, the foot control can be made to work similarly for the right-footed surgeon or the left-footed surgeon. The assignment of functions may also change as the setup of the surgical device changes. For example, the primary linear control may control linear aspiration in one setting and linear phacoemulsification power in another.

Illustration of Functions During Operation

In use of the foot pedal control during surgery by the use of the microsurgical system and its several modules, foot pedal 2326 is utilized in pitch and yaw. The pitch and yaw may control two separate linear functions simultaneously, so that the system may be said to be a dual-linear system. When so configured in a dual linear mode, the aspiration function, for example, is preferably always controlled by pitch action of the foot pedal and another linear function, such as phacoemulsification, controlled linearly by yaw action of the foot pedal. The yaw movement is also usable to simulate left/right side switching actions that activate functions, e.g., enabling vitrectomy cutter to one side, reflux to an opposite side. And, as noted above, the detent levels provided by magnetic particle brake 2356 are fully programmable in pitch movement.

Illustration of Reprogrammable Features and Functions

Figure 12:
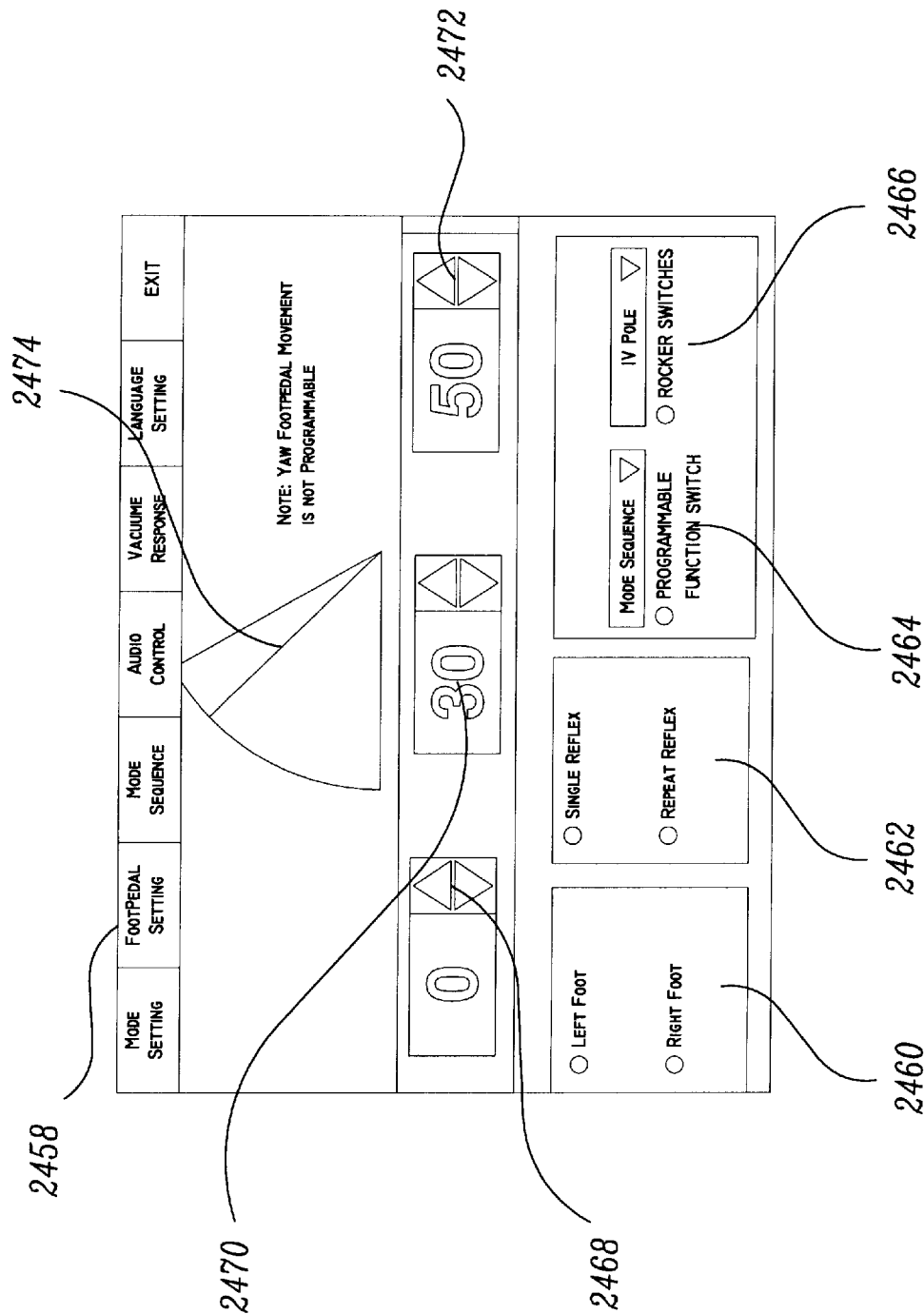
FIG. 12 is an exemplary screen display depicting screen settings and displays appropriate for reconfiguring the operation of the foot control.

Referring to FIG. 12, an exemplary screen display of the microsurgical system 1 shows screen settings and displays appropriate for reconfiguring the operation of the foot control. Here it will be understood that with such touch-screen display, the user touches the desired video-displayed "button" or arrow-indicator on touch-responsive screen 255, as appropriate, for effecting a change.

On the screen display reference character 2456 indicates a touch area for providing foot pedal settings and corresponding display on the screen 255, as here depicted. Reference character 2458 indicates a touch-screen display area with display buttons for selection of left-footed or right-footed operation.

At 2462 is shown a panel with display buttons for selecting single reflux or repeat reflux when the foot pedal is yawed for reflux operation. A switch settings panel 2464 includes display button for allowing the programmable function switch (mode switch 2342) to be selected from a software-defined list for use; and here is shown as having its mode sequence enabled.

As an example of mode sequencing accordingly provided, the mode switch when pressed will then cycle from one mode to the next. Thus, in cataract surgery, tapping the mode switch button 2342 will cycle from a selected one of the bipolar coagulation function, to an aspiration function, to a phaco-emulsification modes, to a selected aspiration mode once more, and then recycle again to the bipolar mode. Or for posterior eye surgery, the mode switch can be selected to transition between a present mode and a previous mode, e.g., from a vitrectomy mode, to a scissors mode, to the vitrectomy mode, etc., so that the foot pedal may then be used in its linear and/or binary control capabilities in the selected mode. As a further example, for a right footed user, the foot pedal may be moved inward (in the direction of the instep) over a linear region of from zero to 100%, relative to its centered position, and when moved outwardly in the lateral aspect may toggle in binary mode to allow reflux operation (i.e., turning reflux on/off).

An adjacent screen panel 2466 has display button for selecting the function from a software-defined list to be controlled by rocker switch 2336, here shown as controlling upward and downward movement of the IV pole.

For selectively controlling pitch activation regions, display areas 2468, 2470, 2472 are provided, for defining activation regions (or what may be termed active regions) of the foot pedal movement in pitch, and for establishing thereby the points at which detents are produced by magnetic particle brake 2356. For example, as here shown, activation region one is set at 0%, activation region two is set at 30%, and activation region three is set at 50%. Display buttons in each of areas 2468, 2470, 2472 are pressed by user touching of the screen to change the degree settings selectively, for bringing about detenting action in accordance with user preference, as hereinabove described with reference to the brake control circuitry. At 2474, a screen display area provides a pictographic display of the brakepedal control activation regions, with detent demarcation, accordingly produced by the latter display button operations.

By comparison, bipolar switch 2342 is not programmed, and will be used its intrinsic binary on/off mode, i.e., enabled when pressed.

Preferably also, foot pedal movement in yaw is not programmable from screen display, but is instead enabled according to whether left foot or right foot operation is selected at panel 2460, and in accordance with programmable function switch selection at panel 2464, e.g., for mode sequence.

What is claimed is:

1. A foot control for use in a microsurgical system having a central processor for defining operating modes and mode sequences for the system, and an electronic display device for display of functions associated with the system, a foot control comprising:

a console;

a foot pedal presented by the console for use by the user of the system during surgery;

means disposing the foot pedal for movement in pitch by the user over a predetermined maximum extent of pitch movement, to selectively control one or more linear functions carried out by the system according to its operating modes and mode sequences;

a control circuit within the console and connected with the microsurgical system in a computer network for data communication with the microsurgical system;

the control circuit electronically supervising foot pedal movements in pitch and for reporting such movements and actuation to the microsurgical system for control accordingly of the microsurgical system in its operating modes;

the control circuit communicating with the system for programming the features and functions of the foot pedal and for permitting user control by changing the pitch of the foot pedal; and the control circuit functioning with the system for defining within the total extent of pitch movement of the foot pedal a plurality of activation regions, and enabling each of the activation regions to be selectively varied in respective arcuate extent over the total extent of pitch movement.

2. A foot control as set forth in claim 1 wherein the control circuit functions with the system for providing electronically controlled detenting of movement of the foot pedal for providing palpable detenting of movement of the foot pedal from one activation region to another activation region, whereby to signal to the user the transition of foot pedal movement from one activation region to another.

3. A foot control as set forth in claim 1 wherein the control circuit comprises an electronically-activated brake interconnected with the foot pedal and selectively energized for detenting action by the control circuit in accordance with predetermined criteria for delimiting extents of pitch movement defined by the detenting.

4. A foot control as set forth in claim 3 wherein the control circuit is controlled by the microsurgical system for selectively varying the extents of each activation region by user-controlled variation upon the electronic display device.

5. A foot control as set forth in claim 3 wherein the control circuit is controlled by the microsurgical system for selectively energizing the brake in accordance with preselectably variable levels of energization.

6. A foot control as set forth in claim 5 wherein detenting between foot pedal activation regions is produced by pulsed energization of the brake, such that a braking pulse provides a corresponding detent.

7. A foot control as set forth in claim 5 wherein detenting between foot pedal activation regions is produced by step-increased energization of the brake corresponding to each detent.

8. A foot control as set forth in claim 5 wherein the foot pedal defines a linear mode of control over each of a plurality of activation regions.

9. A foot control as set forth in claim 5 wherein the control circuit selectively energizes the brake in accordance with preselectably variable levels of energization, in which current through the brake is increased to define a corresponding detent, the control circuit defining a hysteresis band between increasing the brake current and decreasing the brake current if the foot pedal is moved from the detent position to avoid a foot pedal edge point, as would toggle on and off braking force by the brake.

10. A foot control as set forth in claim 3 wherein electronically-activated brake is a magnetic particle brake mechanically coupled to the foot pedal, the control circuit including brake drive circuitry for powering the brake for detenting action, and selectively controllable for establishing a plurality of different brake energization levels defining respective different braking levels.

11. A foot control for use in a microsurgical system having a central processor for defining operating modes and mode sequences for the system, a foot control comprising:

a console;

a foot pedal presented by the console for use by the user of the system during surgery;

means disposing the foot pedal for movement in pitch by the user over a predetermined maximum extent of pitch movement, to selectively control one or more linear functions carried out by the system according to its operating modes and mode sequences;

a control circuit within the console and connected with the microsurgical system in a computer network for data communication with the microsurgical system;

the control circuit electronically supervising foot pedal movements in pitch and for reporting such movements and actuation to the microsurgical system for control accordingly of the microsurgical system in its operating modes;

the control circuit communicating with the system for programming the features and functions of the foot pedal in yaw for permitting user control of operating modes by changing the pitch of the foot pedal;

the control circuit functioning with the system for defining within the total extent of pitch movement of the foot pedal a plurality of activation regions, and enabling the activation regions to be selectively varied in respective arcuate extent;

an electronically-activated brake contained within the console and interconnected with the foot pedal and selectively energizable for detenting action in accordance with predetermined system criteria;

the brake being selectively energizable for controlled detenting of movement of the foot pedal for indicating transition of foot pedal movement from one activation region to another activation region; and the control circuit comprising a brake drive circuit for energizing the brake, including circuit means for providing a current for the brake for braking action, and for rapidly increasing the brake current for rapid engagement of the brake to provide a detenting action without substantial delay.

12. A foot control as set forth in claim 11 wherein the brake is a magnetic particle brake having a winding for energizing the brake, and the current for the brake is delivered to said winding by a voltage-controlled power supply, the brake drive circuit reducing the brake response time upon braking by first energizing the brake coil winding with a brake drive voltage significantly higher than its normal operating voltage, and when the brake current has reached a required operating value for braking action, reducing the brake drive voltage to a level to maintain an operating current for braking action.

13. A foot control as set forth in claim 12 wherein the brake drive circuit comprises a pulse width modulated drive for the brake, the pulse width being modulated to control operating current for the brake coil winding.

14. A foot control as set forth in claim 12 wherein the pulse width modulated drive is a DC-to-DC switching power supply controlled by voltage feedback from a current loop including the brake coil winding.

15. A foot control as set forth in claim 14 including a sensing resistor in the loop providing pulse width modulation feedback control signal to the power supply to control current in the loop, a further resistor in the loop and solid state switching means for rapidly increasing loop current for brake actuation by bypassing the further resistor.

16. A foot control as set forth in claim 15 wherein the solid state switching means is a FET having main terminals connected across the further resistor, the FET being selectively driven into conductive state to bypass the further resistor for causing rapid brake action by rapidly increasing energization of the brake coil winding, and the FET being selectively returned to a nonconductive state to shunt loop current through the further resistor for causing rapid brake release.

17. A foot control as set forth in claim 15 wherein the solid state switching means is controlled for brake enabling or brake releasing by the control circuit.

18. A foot control as set forth in claim 15 further comprising a switching circuit for selectively applying further resistance in parallel with the sensing resistor for changing its value, whereby to control the feedback signal in a sense for controlling the level of energization of the brake coil winding.

19. A foot control as set forth in claim 15 wherein the switching circuit is a solid state switch selectively controlled by the control circuit for providing a plurality of discrete levels of energization of the brake coil winding, whereby to create different possible detent levels for the foot pedal.

20. A foot control as set forth in claim 15 wherein the control circuit is controlled by the microsurgical system for selectively energizing the brake in accordance with preselectably variable levels of energization.

21. A foot control as set forth in claim 15 wherein the control circuit selectively energizes the brake in accordance with preselectably variable levels of energization, in which current through the brake is increased to define a corresponding detent, the control circuit defining a hysteresis band between increasing the brake current and decreasing the brake current if the foot pedal is moved from the detent position to avoid a foot pedal edge point, as would toggle on and off braking force by the brake.

22. A foot control as set forth in claim 11 wherein electronically-activated brake is a magnetic particle brake mechanically coupled to the foot pedal, the control circuit including brake drive circuitry for powering the brake for detenting action, and selectively controllable for establishing a plurality of different brake energization levels defining respective different braking levels.

23. A foot control as set forth in claim 22 wherein detenting between foot pedal activation regions is produced by pulsed energization of the brake, such that a braking pulse provides a corresponding detent.

24. A foot control as set forth in claim 15 wherein detenting between foot pedal activation regions is produced by step-increased energization of the brake corresponding to each detent.

* * * * *